US012558409B2

(12) United States Patent (10) Patent No.: US 12,558,409 B2

Brazel et al. (45) Date of Patent: Feb. 24, 2026

(54) STREPTOCOCCAL VACCINE FORMULATIONS AND USES THEREOF

(71) Applicant: GPN Vaccines Ltd, Yarralumla (AU)

(72) Inventors: Erin Bridget Brazel, Woodville West (AU); Mohammed Alsharifi, Elizabeth Park (AU); Shannon Christa David, Brompton (AU); Timothy Raymond Hirst, Yarralumla (AU); James Cleland Paton, Parkside (AU)

(73) Assignee: GPN Vaccines Ltd, Yarralumla (AU)

( * ) Notice: Subject to any disclaimer, the term of this patent is extended or adjusted under 35 U.S.C. 154(b) by 279 days.

(21) Appl. No.: 17/327,513

(22) Filed: May 21, 2021

(65) Prior Publication Data

US 2021/0361757 A1 Nov. 25, 2021

Related U.S. Application Data

(60) Provisional application No. 63/028,971, filed on May 22, 2020.

(51) Int. Cl.
| | |
|---|---|
| *A61K 39/09* | (2006.01) |
| *A61K 39/00* | (2006.01) |
| *C12N 1/20* | (2006.01) |
| *C12N 15/09* | (2006.01) |
| *C12R 1/46* | (2006.01) |

(52) U.S. Cl.
CPC .............. *A61K 39/092* (2013.01); *C12N 1/20* (2013.01); *C12N 15/09* (2013.01); *A61K 2039/521* (2013.01); *A61K 2039/522*
(2013.01); *A61K 2039/54* (2013.01); *C12N 2500/05* (2013.01); *C12N 2500/30* (2013.01); *C12N 2537/10* (2013.01); *C12R 2001/46* (2021.05)

(58) Field of Classification Search
None
See application file for complete search history.

(56) References Cited

U.S. PATENT DOCUMENTS 10,821,168 B2 * 11/2020 Babb ...................... A61P 31/04

OTHER PUBLICATIONS

Tseng et al (Infect Immun Mar. 2002;70(3):1635-9). (Year: 2002).*
Martin et al. Molecular Microbiology , vol. 104, No. 2, pp. 334-348, Jan. 2017 (Year: 2017).*
David et al (Immunology and Cell Biology 97(8): 726-739; Apr. 29, 2019. (Year: 2019).*
Bortoni, et al., "The pneumococcal response to oxidative stress includes a role for Rgg", Microbiology 155:4123-4134 (Sep. 2009).
Berry, et al., "Sequence Heterogeneity of PsaA, a 37-Kilodalton Putative Adhesin Essential for Virulence of Streptococcus pneumoniae", Infection and Immunity 64(12):5255-5262 (Dec. 1996),.

* cited by examiner

*Primary Examiner* — Jana A Hines
*Assistant Examiner* — Khatol S Shahnan Shah
(74) *Attorney, Agent, or Firm* — Myers Bigel, P.A.

(57) ABSTRACT

The present invention relates to streptococcal vaccine formulations and their use in generating immunity against streptococcal infection.

15 Claims, 10 Drawing Sheets

Specification includes a Sequence Listing.

GPN-001
1. Incorporated erythromycin resistance cassette into *psa* region
GPN-001 Δ*psa*::*ery*<sup>R</sup>
2. Transformed GPN-001 Δ*psa*::*ery*<sup>R</sup> with *psaC*-deficient PCR product spanning
*psa* region (+/- 1kb DNA) to replace erythromycin resistance cassette
3. Generation of GPN-001 Δ*psaC* confirmed by antibiotic resistance profile, PCR
and DNA size analysis
FIG. 1

FIG. 5A
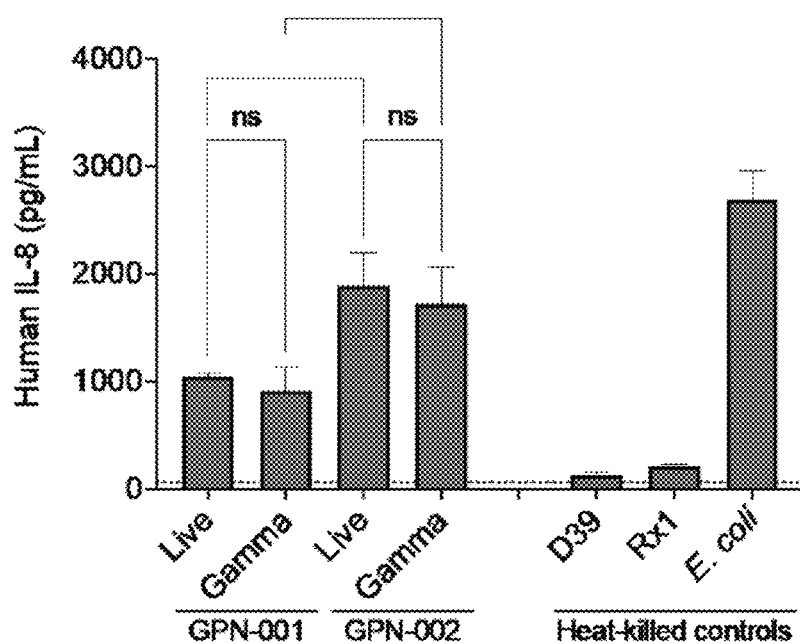
FIG. 5B
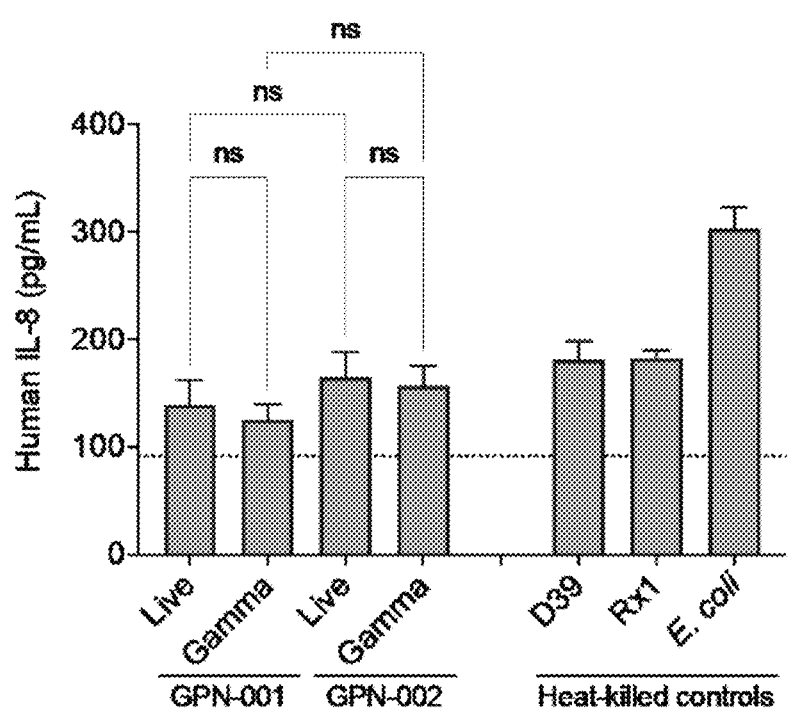

GPN-001
Immune Sera

GPN-002
Immune Sera

FIG. 7A     Serotype 2 Challenge
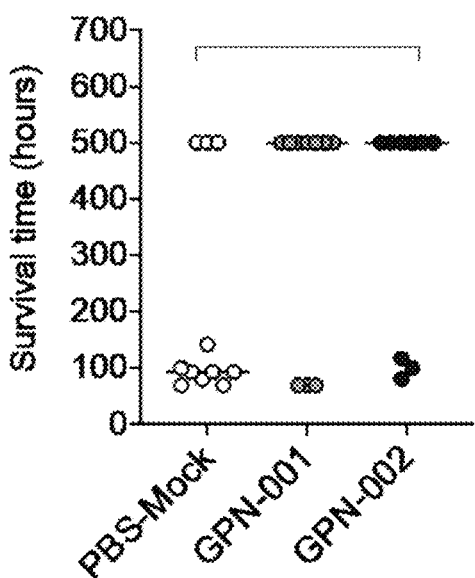
FIG. 7B     Serotype 6A Challenge
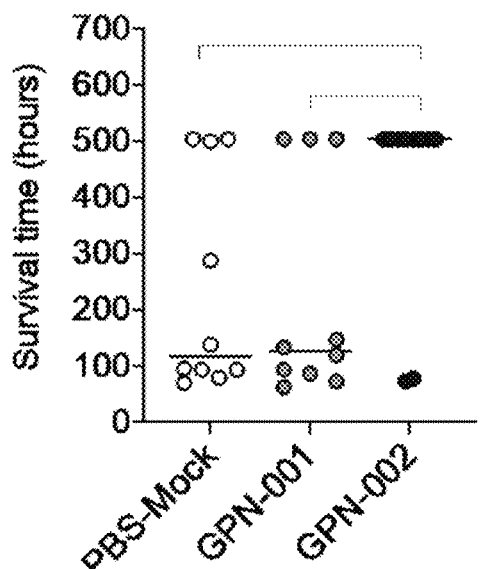

SEQUENCE LISTING

```
<160> NUMBER OF SEQ ID NOS: 6

<210> SEQ ID NO 1
<211> LENGTH: 5171
<212> TYPE: DNA
<213> ORGANISM: Streptococcus pneumoniae

<400> SEQUENCE: 1
ttgaagaagt catccaaagg tagggcaggc gcgaatttct tgaaatcttc gtaagaatat        60
ggatgataga gtttagcata ttctgaactt tcttcattag agagcaccac tgccgcaact       120
cggcggtcca attcaagtct tttttctagc aagtcttcaa tttcttcatc agagaaatca       180
taagccttga ggagatttgc gctgctttct ttccaaagag tcaagagctc ttcgcgctga       240
ggatgttctt ctgcatagta ggtcgtatct ggcaagattg tgcttggagc gctagcccat       300
agaacattga ttctagcatc cataaagtct ggcgatacac caaaaggaag gaagtttggt       360
tttcctgcaa gctcaaactc tgctagttta gctgtaaaat ccgcaaaagt ttccaattct       420
tggaattctt taaggagtgg taagacaggt gtgataccgt cagcttctct cttgtcaaaa       480
tcacgaacta ggcggtggta tttgacaaag ttttccaaga tagcatcctc aggcacttct       540
tcacctgcta accacttgtc tgttgtcgcc aacatcaggt cttcaatttc ctggtctaaa       600
tcaacaaaac ctcctgtttg agacttatct gctgggattt cagctgtctg ttgccattct       660
ccattgatag catcataaaa atcatcttga taacgtgtca tcttgttctc gctttcattt       720
gtatttgcat ttatcttaac aaaaatcact agggaatgca attaataacc atttaactat       780 tatttttttag ctattataaa aaatctttcc atgataaaac gcataattcc aagttttta       840 cacttgatac tatgcgtttt ataatttaga aatttatcct gaaagttatc tttagaatct       900
atttttcagt tattatttta atttttttcaa aaattaactt gacttaatttt ttttttttaat      960 gtatattaag agacaggagg aatacaagtt tatgatacgt atcgaaaacc tcagtgtctc      1020
ctacaaagaa acgttggcac ttaaggatat ttcactagtg ctccatggac caacaattac      1080
cggcatcatt ggtccaaacg gcgctgggaa atcaacacta ttaaaaggta tgctgggaat      1140
tatcccacat caaggtcagg catttctcga tgacaaggaa gttaaaaaat ccttacaccg      1200
aattgcctat gtcgaacaaa aaatcaatat cgactacaac tttcccatca aggtcaagga      1260
atgcgtctcg ttaggactat ttccctctat tcctctcttt cgaagtttaa aggctaaaca      1320
ttggaagaaa gtgcaagagg cccttgaaat cgtcggccta gctgactacg ctgaacgtca      1380
aattagtcaa ctgtctggag gtcaattcca gcgggtcttg attgccagat gtttggtgca      1440
ggaagccgac tatatcctct tggatgaacc ctttgctggg attgactctg tcagtgagga      1500
aatcatcatg aatacgctga gagatttgaa aaaagctggg aagacggttc tcatcgttca      1560
ccacgacctc agcaagattc cccactactt cgatcaagtc ttacttgtca atcgagaagt      1620
gattgccttt ggtccaacaa aagaaacttt taccgaaacc aatctaaaag aagcttacgg      1680
taatcaactc tttttcaatg gaggtgacct atgattgcag aatttatcga tggattgcaa      1740
```

```
aaattccatt tcctacaaaa tgccttgata acagctattg tcgtcgggat tgtagctgga     1800
gctgtgggat gtttcattat tctacgcggg atgtcactca tgggagatgc catttcacat     1860
gctgtcttac caggtgtagc cctctccttc atcttgggcc ttgacttctt tatcggagcc     1920
attgtctttg gattgctagc tgccatcatc attacctaca tcaaaggaaa ctcgattatc     1980
aaaagcgata ccgccatcgg cattaccttt tcttctttct tagccctcgg tatcatcttg     2040
attggtgtcg ctaaaagttc aactgacctt ttccatatcc tttttggtaa tatcctggcc     2100
gtccaagata cggatatgtt tattactatg ggtgtggggg cagccatcct cttgttaatc     2160
tggattttct tcaagcaact cttgataact tcctttgatg aactcttggc taaagccatg     2220
ggaatgcctg tcaatttcta tcactacctt ctcatggtac tcctgactct cgtgtctgtg     2280
acagccatgc aaagtgtcgg aactatcctg attgtagcca tgctgattac cccagctgca     2340
actgcttatc tgtatgctaa tagtctgaaa agcatgattt tcctttcctc aaccttcgga     2400
gctactgctt cagttttggg actctttatt ggctatagtt ttaatgttgc ggcaggttct     2460
agtatcgtgc ttacagctgc tagtttcttt ctcattagct tctttatcgc tcccaaacaa     2520
cgatatttga aactgaaaaa taaacatttg ttaaaataag gggcaaagcc ctaataaatt     2580
ggaggatcta atgaaaaaat taggtacatt actcgttctc tttctttctg caatcattct     2640
tgtagcatgt gctagcggaa aaaaagatac aacttctggt caaaaactaa aagttgttgc     2700
tacaaactca atcatcgctg atattactaa aaatattgct ggtgacaaaa ttgaccttca     2760
tagtatcgtt ccgattgggc aagacccaca cgaatacgaa ccacttcctg aagacgttaa     2820
gaaaacttct gaggctgatt tgattttcta taacggtatc aaccttgaaa caggtggcaa     2880
tgcttggttt acaaaattgg tagaaaatgc caagaaaact gaaaacaaag actacttcgc     2940
agtcagcgac ggcgttgatg ttatctacct tgaaggtcaa aatgaaaaag gaaaagaaga     3000
cccacacgct tggcttaacc ttgaaaacgg tattattttt gctaaaaata tcgccaaaca     3060
attgagcgcc aaagacccta acaataaaga attctatgaa aaaaatctca agaatatac     3120 tgataagtta gacaaacttg ataaagaaag taaggataaa tttaataaga tccctgctga     3180
aaagaaactc attgtaacca gcgaaggagc attcaaatac ttctctaaag cctatggtgt     3240
tccaagtgcc tacatctggg aaatcaatac tgaagaagaa ggaactcctg aacaaatcaa     3300
gaccttggtt gaaaaacttc gccaaacaaa agttccatca ctctttgtag aatcaagtgt     3360
ggatgaccgt ccaatgaaaa ctgtttctca agacacaaac atcccaatct acgcacaaat     3420
ctttactgac tctatcgcag aacaaggtaa agaaggcgac agctactaca gcatgatgaa     3480
atacaacctt gacaagattg ctgaaggatt ggcaaaataa gcctctgaaa aacgtcattc     3540
tcatgtgagc tggcgttttt tctatgccca catttccggt caaatcattg gaaaattctg     3600
actgtttcag atacaatgga agaaaaaaga ttggagtatc ctatggtaac ttttctcgga     3660
aatcctgtga gctttacagg taaacaacta caagtcggcg acaaggcgct tgattttct     3720 cttactacaa cagatctttc taaaaaatct ctggctgatt ttgatggcaa gaaaaaagtc     3780
ttgagtgtcg ttccttctat cgatacaggc atctgctcaa ctcaaacacg tcgttttaat     3840
gaagaattgg ctggactgga caacacggtc gtattgactg tttcaatgga cctaccttt    3900 gctcaaaaac gttggtgcgg tgctgaaggc cttgacaatg ccattatgct ttcagactac     3960
tttgaccatt ctttcgggcg cgattatgcc ctcttgatca acgaatggca cctattagca     4020
cgcgcagtct ttgtcctcga tactgacaat acgattcgct acgttgaata cgtggataat     4080
```

-continued

```
atcaattctg agccaaactt cgaagccgca attgcagctg ctaaagccct atagaaaaaa   4140
tcctctgtca caaagagttc cctgctcttt gaaacggagg attttgaat attagtaaat    4200 agaagttcaa tcagctaaaa ataactacct tactctacag atttcagggc ttctaacata   4260
tcaacctttc tcagataata attgacgaag aaaccaagca aggtcaaaat gatgcttact   4320
gctgccactg ggattacata gacttcccag cctacctgcg gataaaagag aatagtcgca   4380
ggcgaaatca tttgaatcaa aaattggtgt aaatagaaac cagctaccag accaagtacg   4440
attcccacaa gggatagcac aatcgtctca cggtaaatgt agagggtgac ttcattatta   4500
tgaaaaccaa gaaccttggt agtggagagt tcacggattc tctcagctac gttgatattg   4560
gtcagattgt aaaggatgac aatagctaat agaaccgata cgatgaccaa gatggtcatg   4620
gtctgattga gtgagctagc gacagagtcg aagagtcgaa tggctgaagc attttggaca   4680
acgctggaca ccgcagattg actcataagc aagcccgcct gactttcgat actagttgca   4740
ctggtatccc ttaatgagac cagataagtg ttggcttggg gtagctgtcc gtaaagttgc   4800
tcatagctag cctgactcat ataaataaag tgaccaacgt agttctcagt aatagcagcg   4860
acctttagtt ccttaccttc aatttctaaa gtctgcccaa ccttgacacc tgccagctgg   4920
gcgagtttag ctgtaataac gatgccatct tttaatgtca gctcctgctg atgatgttga   4980
agatggataa agggagtcaa atcttccttc tctatcatca taagagtaat gttttgaaga   5040
ctagccttgc ctttgaaatc cttgtctagc gttttagaat agattttctg gtaggctagt   5100
atctcctgcc ctttcaacac ttctgctagc tctaccttgt cctgattggt cgcactagga   5160
ttttcagaga c                                                        5171
```

```
<210> SEQ ID NO 2
<211> LENGTH: 4399
<212> TYPE: DNA
<213> ORGANISM: Artificial Sequence
<220> FEATURE:
<223> OTHER INFORMATION: Streptococcus pneumoniae strain sequence with
     psaC gene deleted

<400> SEQUENCE: 2
```

```
ttgaagaagt catccaaagg tagggcaggc gcgaatttct tgaaatcttc gtaagaatat     60
ggatgataga gtttagcata ttctgaactt tcttcattag agagcaccac tgccgcaact    120
cggcggtcca attcaagtct tttttctagc aagtcttcaa tttcttcatc agagaaatca    180
taagccttga ggagatttgc gctgctttct ttccaaagag tcaagagctc ttcgcgctga    240
ggatgttctt ctgcatagta ggtcgtatct ggcaagattg tgcttggagc gctagcccat    300
agaacattga ttctagcatc cataaagtct ggcgatacac caaaaggaag gaagtttggt    360
tttcctgcaa gctcaaactc tgctagttta gctgtaaaat ccgcaaaagt ttccaattct    420
tggaattctt taaggagtgg taagacaggt gtgataccgt cagcttctct cttgtcaaaa    480
tcacgaacta ggcggtggta tttgacaaag ttttccaaga tagcatcctc aggcacttct    540
tcacctgcta accacttgtc tgttgtcgcc aacatcaggt cttcaatttc ctggtctaaa    600
tcaacaaaac ctcctgtttg agacttatct gctgggattt cagctgtctg ttgccattct    660
ccattgatag catcataaaa atcatcttga taacgtgtca tcttgttctc gctttcattt    720
gtatttgcat ttatcttaac aaaaatcact agggaatgca attaataacc atttaactat    780 tatttttag ctattataaa aaatctttcc atgataaaac gcataattcc aagtttttta    840
cacttgatac tatgcgtttt ataatttaga aatttatcct gaaagttatc tttagaatct    900
```

-continued

```
attttttcagt tattatttta attttttcaa aaattaactt gacttaattt ttttttttaat      960 gtatattaag agacaggagg aatacaagtt tatgatacgt atcgaaaacc tcagtgtctc     1020
ctacaaagaa acgttggcac ttaaggatat ttcactagtg ctccatggac caacaattac     1080
cggcatcatt ggtccaaacg gcgctgggaa atcaacacta ttaaaaggta tgctgggaat     1140
tatcccacat caaggtcagg catttctcga tgacaaggaa gttaaaaaat ccttacaccg     1200
aattgcctat gtcgaacaaa aaatcaatat cgactacaac tttcccatca aggtcaagga     1260
atgcgtctcg ttaggactat ttccctctat tcctctcttt cgaagtttaa aggctaaaca     1320
ttggaagaaa gtgcaagagg cccttgaaat cgtcggccta gctgactacg ctgaacgtca     1380
aattagtcaa ctgtctggag gtcaattcca gcgggtcttg attgccagat gtttggtgca     1440
ggaagccgac tatatcctct tggatgaacc ctttgctggg attgactctg tcagtgagga     1500
aatcatcatg aatacgctga gagatttgaa aaaagctggg aagacggttc tcatcgttca     1560
ccacgacctc agcaagattc cccactactt cgatcaagtc ttacttgtca atcgagaagt     1620
gattgccttt ggtccaacaa aagaaacttt taccgaaacc aatctaaaag aagcttacgg     1680
taatcaactc ttttttcaatg gaggtgacct atgattgcag aatttatcga tggaatcgct     1740
cccaaacaac gatatttgaa actgaaaaat aaacatttgt taaaataagg ggcaaagccc     1800
taataaattg gaggatctaa tgaaaaaatt aggtacatta ctcgttctct ttctttctgc     1860
aatcattctt gtagcatgtg ctagcggaaa aaaagataca acttctggtc aaaaactaaa     1920
agttgttgct acaaactcaa tcatcgctga tattactaaa aatattgctg gtgacaaaat     1980
tgaccttcat agtatcgttc cgattgggca agacccacac gaatacgaac cacttcctga     2040
agacgttaag aaaacttctg aggctgattt gattttctat aacggtatca accttgaaac     2100
aggtggcaat gcttggttta caaaattggt agaaaatgcc aagaaaactg aaaacaaaga     2160
ctacttcgca gtcagcgacg gcgttgatgt tatctacctt gaaggtcaaa atgaaaaagg     2220
aaaagaagac ccacacgctt ggcttaacct tgaaaacggt attattttttg ctaaaaatat     2280 cgccaaacaa ttgagcgcca aagaccctaa caataaagaa ttctatgaaa aaaatctcaa     2340
agaatatact gataagttag acaaacttga taaagaaagt aaggataaat ttaataagat     2400
ccctgctgaa aagaaactca ttgtaaccag cgaaggagca ttcaaatact tctctaaagc     2460
ctatggtgtt ccaagtgcct acatctggga aatcaatact gaagaagaag gaactcctga     2520
acaaatcaag accttggttg aaaaacttcg ccaaacaaaa gttccatcac tctttgtaga     2580
atcaagtgtg gatgaccgtc caatgaaaac tgtttctcaa gacacaaaca tcccaatcta     2640
cgcacaaatc tttactgact ctatcgcaga acaaggtaaa gaaggcgaca gctactacag     2700
catgatgaaa tacaaccttg acaagattgc tgaaggattg gcaaaataag cctctgaaaa     2760
acgtcattct catgtgagct ggcgtttttt ctatgcccac atttccggtc aaatcattgg     2820
aaaattctga ctgtttcaga tacaatggaa gaaaaaagat tggagtatcc tatggtaact     2880
tttctcggaa atcctgtgag ctttacaggt aaacaactac aagtcggcga caaggcgctt     2940 gattttttctc ttactacaac agatctttct aaaaaaatctc tggctgattt tgatggcaag     3000
aaaaaagtct tgagtgtcgt tccttctatc gatacaggca tctgctcaac tcaaacacgt     3060
cgttttaatg aagaattggc tggactggac aacacggtcg tattgactgt ttcaatggac     3120 ctacctttttg ctcaaaaacg ttggtgcggt gctgaaggcc ttgacaatgc cattatgctt     3180
tcagactact ttgaccattc tttcgggcgc gattatgccc tcttgatcaa cgaatggcac     3240
ctattagcac gcgcagtctt tgtcctcgat actgacaata cgattcgcta cgttgaatac     3300
```

-continued

```
gtggataata tcaattctga gccaaacttc gaagccgcaa ttgcagctgc taaagcccta    3360
tagaaaaaat cctctgtcac aaagagttcc ctgctctttg aaacggagga tttttgaata    3420
ttagtaaata gaagttcaat cagctaaaaa taactacctt actctacaga tttcagggct    3480
tctaacatat caacctttct cagataataa ttgacgaaga aaccaagcaa ggtcaaaatg    3540
atgcttactg ctgccactgg gattacatag acttcccagc ctacctgcgg ataaaagaga    3600
atagtcgcag gcgaaatcat ttgaatcaaa aattggtgta aatagaaacc agctaccaga    3660
ccaagtacga ttcccacaag ggatagcaca atcgtctcac ggtaaatgta gagggtgact    3720
tcattattat gaaaaccaag aaccttggta gtggagagtt cacggattct ctcagctacg    3780
ttgatattgg tcagattgta aaggatgaca atagctaata gaaccgatac gatgaccaag    3840
atggtcatgg tctgattgag tgagctagcg acagagtcga agagtcgaat ggctgaagca    3900
ttttggacaa cgctggacac cgcagattga ctcataagca agcccgcctg actttcgata    3960
ctagttgcac tggtatccct taatgagacc agataagtgt tggcttgggg tagctgtccg    4020
taaagttgct catagctagc ctgactcata taaataaagt gaccaacgta gttctcagta    4080
atagcagcga cctttagttc cttaccttca atttctaaag tctgcccaac cttgacacct    4140
gccagctggg cgagtttagc tgtaataacg atgccatctt ttaatgtcag ctcctgctga    4200
tgatgttgaa gatggataaa gggagtcaaa tcttccttct ctatcatcat aagagtaatg    4260
ttttgaagac tagccttgcc tttgaaatcc ttgtctagcg ttttagaata gattttctgg    4320
taggctagta tctcctgccc tttcaacact tctgctagct ctaccttgtc ctgattggtc    4380
gcactaggat tttcagaga                                                 4399

<210> SEQ ID NO 3
<211> LENGTH: 20
<212> TYPE: DNA
<213> ORGANISM: Artificial Sequence
<220> FEATURE:
<223> OTHER INFORMATION: Forward primer for amplification of prtA gene
      sequence component

<400> SEQUENCE: 3
aagaaaagca ggcattccaa                                                  20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for amplification of prtA gene
      sequence component

<400> SEQUENCE: 4
gcagaagcga ccgctatcgc                                                  20

<210> SEQ ID NO 5
<211> LENGTH: 20
<212> TYPE: DNA
<213> ORGANISM: Artificial Sequence
<220> FEATURE:
<223> OTHER INFORMATION: Forward primer for normalising levels of prtA
      gene transcription to the gyrase A gene (gyrA)

<400> SEQUENCE: 5
actggtatcg cggttgggat                                                  20
```

-continued

```
<210> SEQ ID NO 6
<211> LENGTH: 20
<212> TYPE: DNA
<213> ORGANISM: Artificial Sequence
<220> FEATURE:
<223> OTHER INFORMATION: Reverse primer for normalising levels of prtA
      gene transcription to the gyrase A gene (gyrA)

<400> SEQUENCE: 6
acctgatttc cccatgacaa                                          20
```

STREPTOCOCCAL VACCINE FORMULATIONS AND USES THEREOF

CROSS-REFERENCE TO RELATED APPLICATION

The present invention claims the right of priority from U.S. provisional patent application Ser. No. 63/028,971 filed May 22, 2020, the content of which is incorporated herein by cross-reference in its entirety.

STATEMENT REGARDING ELECTRONIC FILING OF A SEQUENCE LISTING

A Sequence Listing in ASCII text format, submitted under 37 C.F.R. § 1.821, entitled 9875.22_ST25.txt, 14,208 bytes in size, generated on May 21, 2021 and filed via EFS-Web, is provided in lieu of a paper copy. This Sequence Listing is hereby incorporated by reference into the specification for its disclosures.

TECHNICAL FIELD

The present invention relates generally to the field of vaccines. More specifically, the present invention relates to streptococcal vaccine formulations and their use in generating immunity against streptococcal infection.

BACKGROUND

*Streptococci* are a genus of spheroidal bacteria belonging to the family Streptococcaceae. There are many different species of *streptococci*, some of which cause disease in humans and animals. Others are important in the manufacture of various fermented products.

Individual streptococcal species are classified into two key groups based on their haemolytic properties (alpha- and beta-haemolytic). Alpha-haemolytic *streptococci* include *Streptococcus pneumoniae* and *Viridans streptococci*. The beta-haemolytic group is made up of Group A and Group B *streptococci*. Group B *streptococci* usually inhabit the digestive system and the vagina of women without adverse effect. Most people quickly develop a natural immunity to Group B *streptococci* although they can cause more serious types of infection in newborn infants. Group A *streptococci* commonly inhabit the throat and skin surface, and are a common cause of infection in adults and children. Although most Group A infections do not usually pose a serious threat to health (e.g. throat infections, cellulitis, impetigo, sinusitis, middle ear infections) Group A *Streptococci* can establish a more serious invasive infection by penetrating deeper into the tissues and organs of the body (e.g. pneumonia, sepsis, meningitis, necrotising fasciitis) and can trigger serious sequelae including acute post-streptococcal glomerulonephritis and acute rheumatic fever. In addition, enterococcal (faecal) streptococcal species occur in significant numbers in the bowel and can cause endocarditis and urinary tract infections.

Group A *Streptococcus* (GAS, *Streptococcus pyogenes*) causes a wide range of acute and chronic clinical issues in humans. GAS infections and adverse consequences are one of the top 10 causes of death from infectious diseases worldwide, with an estimated 0.5 million deaths annually, in all age ranges and commonly in young adults. However, GAS has received little attention in global health programs, and existing tools for prevention are inadequate. High genetic diversity of antigen targets, safety concerns, and lack of consensus on clinical endpoints for establishment of proof of concept have created significant impediments to progress in GAS vaccine development to date.

*Streptococcus pneumoniae* (pneumococcus) is an important human pathogen accounting for significant morbidity and mortality in human and animal populations. It causes serious conditions including pneumonia, meningitis, sinusitis, and otitis media. An estimated 1.6 million people die globally from invasive pneumococcal disease each year and approximately one million of those are children. There are many different serotypes of *S. pneumoniae* (>90) distinguishable on the basis of capsule chemical structure and immunogenicity. The capsular polysaccharide is considered to be an essential virulence factor of *S. pneumoniae* as non-encapsulated strains are virtually absent among *S. pneumoniae* strains that are responsible for invasive pneumococcal disease. Capsular polysaccharides are thus used as vaccine antigens in current pneumococcal vaccines.

Current pneumococcal conjugate vaccines cover only a selected set of serotypes, (e.g. PCV7 (7 serotypes), PCV10 (10 serotypes) and PCV13 (13 serotypes)), but protection is largely restricted to included serotypes. In many populations the introduction of the PCV7 vaccine targeting serotypes 4, 6B, 9V, 14, 18C, 19F, and 23F significantly reduced the burden of pneumococcal disease. However, despite their efficacy against disease caused by targeted vaccine serotypes, serotype replacement often reduces the net effect of vaccination. The emergence of non-vaccine serotypes upon the implementation of pneumococcal conjugate vaccines thus raises a problem.

*Streptococcus agalactiae* (group B *Streptococcus*, GBS) is a leading cause of severe invasive disease in immunocompromised, neonate and elderly individuals worldwide. Despite recent advances in the diagnosis and intrapartum antibiotic prophylaxis (IAP) of GBS infections, it causes serious infections and remains one of the most common causes of neonatal morbidity and mortality. Recent studies have also reported an increasing number of GBS infections in pregnant women and the elderly. Although IAP is effective, it has several limitations, including increasing antimicrobial resistance and late GBS infection after negative antenatal screening. There is currently no vaccine available for this pathogen.

Groups C and G *streptococci* are associated with a similar range of illnesses as *Streptococcus pyogenes*. In children, they are most commonly involved in respiratory tract infections such as pharyngitis. The true incidence of pharyngitis caused by groups C and G *streptococci* is difficult to determine because asymptomatic colonization occurs. Nonetheless, there is compelling evidence implicating group C and G *streptococci* as true causes of pharyngitis. Groups C and G *streptococci* also cause skin and soft tissue infections. They have been shown to colonise the skin and gain access to subcutaneous tissues after skin injury. Other diseases associated with Group C and group G *streptococci* include rheumatic heart disease, and neonatal septicemia.

There is a continued prevalence of pathogenic streptococcal infection causative of a range of conditions including, for example, pharyngitis, pneumonia, wound and skin infections, sepsis, rheumatic fever, glomerulonephritis and endocarditis. While most strains are sensitive to penicillin, macrolide-resistant strains have recently emerged.

A need thus exists for improved streptococcal vaccines capable of preventing streptococcal infection. Streptococcal vaccines capable of inducing immunity against a broader range of serotypes are also desirable.

SUMMARY OF THE INVENTION

The invention relates to an improved streptococcal vaccine that reduces or alleviates at least one deficiency of existing streptococcal vaccines.

The present inventors have unexpectedly identified that the immunity induced by inactivated *Streptococci* is unexpectedly enhanced when intracellular manganese levels of the bacteria are restricted. According to the present invention, the efficacy of streptococcal vaccine preparations can thus be improved by application of this general principle. The restriction of intracellular manganese in streptococcal strains may be achieved by any number of suitable means, non-limiting examples of which are described herein. Immunogenic vaccine compositions and methods for vaccinating against streptococcal infection utilising the compositions are provided.

The present invention relates to at least the following embodiments:

Embodiment 1

A vaccine composition comprising at least one of: (i) attenuated or killed streptococcal bacteria comprising a modification that restricts intracellular levels of manganese ions ($Mn^{2+}$), (ii) attenuated or killed streptococcal bacteria cultured in a manner that restricts levels of intracellular manganese ions ($Mn^{2+}$), (iii) immunogenic components of at least one of: (i) and (ii); wherein the attenuated or killed streptococcal bacteria of (i) and (ii) are capable of expressing a wild-type protein selected from one of: —pneumococcal surface adhesin A (PsaA), —a homolog of pneumococcal surface adhesin A (PsaA).

Embodiment 2

The vaccine composition of embodiment 1, wherein the attenuated or killed streptococcal bacteria are capable of expressing the wild-type protein at equivalent or increased levels as compared to wild-type forms of the streptococcal bacteria.

Embodiment 3

The vaccine composition of embodiment 1, wherein the modification is a defect in manganese ion ($Mn^{2+}$) transport.

Embodiment 4

The vaccine composition of embodiment 3, wherein the modification is selected from at least one of: deletion, attenuation, and reduced expression; of a protein selected from at least one of: a streptococcal ATP-binding cassette protein, and a streptococcal ABC transporter membrane-spanning permease-manganese transport protein.

Embodiment 5

The vaccine composition of embodiment 1, wherein the modification is selected from one of: deletion, attenuation and reduced expression; of a streptococcal gene selected from at least one of: psaB, psaC, and homologs thereof.

Embodiment 6

The vaccine composition of embodiment 1, wherein the modification enhances expression of a streptococcal gene selected from at least one of: psaR, mntE, mgtA, and homologs thereof.

Embodiment 7

The vaccine composition of embodiment 1, wherein the modification is selected from one of: deletion, suppression and enhancement; of a regulatory sequence capable of altering expression of at least one streptococcal gene selected from: psaB, psaC, mntE, mgA, and homologs thereof.

Embodiment 8

The vaccine composition of embodiment 1, wherein the modification is selected from one of: deletion, attenuation and suppression; of at least one streptococcal gene selected from: sczA, czcD, copA, cupA, copY and homologs thereof; to thereby restrict intracellular levels of manganese ions ($Mn^{2+}$) in the bacteria.

Embodiment 9

The vaccine composition of embodiment 1, wherein the modification is overexpression of at least one streptococcal gene selected from: adcA, adcAII, adcC, adcB, and homologs thereof; to thereby restrict intracellular levels of manganese ions ($Mn^{2+}$) in the bacteria.

Embodiment 10

The vaccine composition of embodiment 1, wherein the attenuated or killed streptococcal bacteria were cultured with an ionophore to thereby increase cellular uptake of cations selected from at least one of: $Zn^{2+}$, $Cu^{2+}$, $Co^{2+}$, $Ni^{2+}$, $Fe^{2+}$, and $Cd^{2+}$.

Embodiment 11

The vaccine composition of embodiment 10, wherein the ionophore is selected from at least one of: pyrithione, 8-hydroxyquinoline, and an analogue thereof.

Embodiment 12

The vaccine composition of embodiment 1, wherein the attenuated or killed streptococcal bacteria were cultured in media comprising cations that compete with manganese ion binding sites on the bacteria.

Embodiment 13

The vaccine composition of embodiment 12, wherein the cations comprise at least one of $Zn^{2+}$, $Cu^{2+}$, $Co^{2+}$, $Ni^{2+}$, $Fe^{2+}$, and $Cd^{2+}$.

Embodiment 14

The vaccine composition of embodiment 12, wherein the cations interact with a streptococcal protein selected from: MgtA riboswitch and homologs thereof; to thereby alter regulation of manganese transport genes in the bacteria.

5

Embodiment 15

The vaccine composition of embodiment 12, wherein the cations interact with a streptococcal protein selected from: MgtA riboswitch and homologs thereof; to thereby increase cellular uptake of the cations in the bacteria.

Embodiment 16

The vaccine composition of embodiment 12, wherein the attenuated or killed streptococcal bacteria were cultured in media comprising a molar excess of the cations sufficient to inhibit PsaA protein function.

Embodiment 17

The vaccine composition of embodiment 1, wherein the attenuated or killed streptococcal bacteria were cultured with at least one of: a chelating agent, and an adsorption agent; to thereby reduce the availability of manganese ions to the bacteria.

Embodiment 18

The vaccine composition of embodiment 17, wherein the agent is selected from at least one of: Ethylenediaminetetraacetic acid (EDTA), trans-1,2-Diaminocyclohexane-N,N, N',N'-tetraacetic acid (CyDTA), N,N,N',N'-tetrakis(2-pyridinylmethyl)-1,2-ethanediamine (TPEN), and Calprotectin.

Embodiment 19

The vaccine composition of embodiment 17, wherein the attenuated or killed streptococcal bacteria were cultured in media pre-treated with Chelex 100 cation chelating resin.

Embodiment 20

The vaccine composition of embodiment 1, wherein the attenuated or killed streptococcal bacteria were cultured in any of: —media without manganese ions, —media depleted of manganese ions, —media with minimal manganese ions sufficient to support growth of the bacteria.

Embodiment 21

The vaccine composition of embodiment 1, wherein the attenuated or killed streptococcal bacteria were cultured in media comprising an antagonist of at least one streptococcal protein selected from: PsaA, PsaB, PsaC, PsaR, MntE, and homologs thereof.

Embodiment 22

The vaccine composition of embodiment 1, wherein the attenuated or killed streptococcal bacteria were cultured in media comprising an antagonist of a regulatory sequence capable of altering expression of at least one streptococcal gene selected from: psaB, psaC, psaR, mntE, mgtA, and homologs thereof.

Embodiment 23

The vaccine composition of embodiment 1, wherein the modification arises from at least one of: altering chromosomal DNA of the bacteria, transformation of the bacteria with a plasmid, culturing the bacteria under selective pressure, knocking down a gene of the bacteria, and introducing a transposon into DNA of the bacteria.

Embodiment 24

The vaccine composition of embodiment 1, wherein the attenuated or killed streptococcal bacteria were killed by at least one of: chemical treatment, thermal treatment, radiation, high hydrostatic pressure, pulsed electric field, ultra-short pulsed laser, ultrasound under pressure, and microbial inactivation.

Embodiment 25

The vaccine composition of embodiment 24, wherein the chemical inactivation comprises inactivation using at least one of: a cross-linking agent, and an alkylating agent.

Embodiment 26

The vaccine composition of embodiment 25, wherein the cross-linking agent is formalin.

Embodiment 27

The vaccine composition of embodiment 25, wherein the alkylating agent is beta-propiolactone.

Embodiment 28

The vaccine composition of embodiment 24, wherein the radiation comprises at least one of: ultraviolet, photon, proton, heavy ion, and low-energy electron irradiation.

Embodiment 29

The vaccine composition of embodiment 28, wherein the photon radiation comprises gamma irradiation.

Embodiment 30

The vaccine composition of embodiment 1, wherein the attenuated or killed streptococcal bacteria further comprise a defect in at least one streptococcal gene selected from: a gene encoding a DNA alkylation repair protein, a gene encoding hemolysin, a gene encoding pneumolysin, a gene encoding autolysin, and a gene encoding DNA polymerase IV.

Embodiment 31

The vaccine composition of embodiment 1, wherein the attenuated or killed streptococcal bacteria further comprise a defect in at least one streptococcal gene selected from: adcR, cibAB, hexA, hexB, ply, luxS, lvtA, mutS, prtA, radC, recA, recF, recN, recO, ritR, uvrA, uvrB, uvrC, uvrD, and homologs thereof.

Embodiment 32

The vaccine composition of embodiment 1, wherein the attenuated or killed streptococcal bacteria are further modified to overexpress at least one of: PspA, PitA, PiuA, PiaA, AdcA, AdcAII, PhtA, PhtB, PhtD, PhtE, PcpA, CbpA, RrgA, RrgB, RrgC, StkP, PrtA and homologs thereof.

Embodiment 33

The vaccine composition of embodiment 1, wherein the attenuated or killed streptococcal bacteria are not capable of producing a polysaccharide capsule.

Embodiment 34

The vaccine composition of embodiment 1, wherein the attenuated or killed streptococcal bacteria are of a single streptococcal species or serotype.

Embodiment 35

The vaccine composition of embodiment 1, wherein the attenuated or killed streptococcal bacteria comprise or consist of *Streptococcus pneumoniae* that are not psaA deletion mutants.

Embodiment 36

The vaccine composition of embodiment 1, wherein the attenuated or killed streptococcal bacteria comprise at least one of: *Streptococcus agalactiae, Streptococcus bovis, Streptococcus canis, Streptococcus dysgalactiae, Streptococcus equi, Streptococcus equinus, Streptococcus equisimilis, Enterococcus faecalis, Enterococcus faecium, Streptococcus iniae, S. milleri, Streptococcus mutans, Streptococcus pneumoniae, Streptococcus pyogenes, Streptococcus salivarius. Streptococcus sanguinis, Streptococcus suis*, and *Streptococcus uberis*.

Embodiment 37

The vaccine composition of embodiment 1, further comprising at least one of: an adjuvant, a pharmaceutically acceptable excipient, and a pharmaceutically acceptable carrier.

Embodiment 38

A method for inducing a cross-protective immune response in a subject against a plurality of serotypes from a given streptococcal species, the method comprising administering the vaccine composition of embodiment 1 to the subject to thereby induce the cross-protective immune response.

Embodiment 39

The method of embodiment 38, wherein the cross-protective immune response comprises at least one of: a Toll-like receptor (TLR)-mediated innate immune response, a Toll-like receptor 2 (TLR2)-mediated innate immune response, a Toll-like receptor 9 (TLR9)-mediated innate immune response.

Embodiment 40

The method of embodiment 38, wherein the vaccine is administered to the subject by at least one of: intranasal, intravenous, intramuscular, subcutaneous, oral, transmucosal, and transdermal administration.

Embodiment 41

The method of embodiment 38, wherein the vaccine composition comprises a single species or serotype of streptococcal bacteria.

Embodiment 42

The method of embodiment 41, wherein the single species of streptococcal bacteria is *Streptococcus pneumoniae.*

Embodiment 43

The method of embodiment 38, wherein the bacteria of the vaccine composition are killed by at least one of: chemical treatment, thermal treatment, radiation, high hydrostatic pressure, pulsed electric field, ultrashort pulsed laser, ultrasound under pressure, and microbial inactivation.

Embodiment 44

A method for preventing an infection by streptococcal bacteria in a subject, the method comprising administering to the subject a vaccine composition comprising at least one of: (i) attenuated or killed streptococcal bacteria comprising a modification that restricts intracellular levels of manganese ions ($Mn^{2+}$), (ii) attenuated or killed streptococcal bacteria cultured in a manner that restricts levels of intracellular manganese ions ($Mn^{2+}$), (iii) immunogenic components of at least one of: (i) and (ii); wherein the attenuated or killed streptococcal bacteria of (i) and (ii) are capable of expressing a wild-type protein selected from one of: —pneumococcal surface adhesin A (PsaA), —a homolog of pneumococcal surface adhesin A (PsaA); to thereby prevent the infection in the subject.

Embodiment 45

The method of embodiment 44, wherein the method prevents infection by a plurality of different streptococcal serotypes.

Embodiment 46

The method of embodiment 44, wherein the method induces a Toll-like receptor (TLR)-mediated innate immune response in the subject.

Embodiment 47

The method of embodiment 44, wherein the method induces a Toll-like receptor 2 (TLR2)-mediated innate immune response in the subject.

Embodiment 48

The method of embodiment 44, wherein the method induces a Toll-like receptor 9 (TLR9)-mediated innate immune response in the subject.

Embodiment 49

The method of embodiment 44, wherein the vaccine is administered to the subject by at least one of: intranasal, intravenous, intramuscular, subcutaneous, oral, transmucosal, and transdermal administration.

Embodiment 50

The method of embodiment 44, wherein the vaccine composition comprises a single species or serotype of streptococcal bacteria.

Embodiment 51

The method of embodiment 44, wherein the attenuated or killed streptococcal bacteria are capable of expressing the wild-type protein at equivalent or increased levels as compared to wild-type forms of the streptococcal bacteria.

Embodiment 52

The method of embodiment 44, wherein the modification is a defect in manganese ion ($Mn^{2+}$) transport.

Embodiment 53

The method of embodiment 52, wherein the modification is selected from at least one of: deletion, attenuation, and reduced expression; of a protein selected from at least one of: a streptococcal ATP-binding cassette protein, and a streptococcal ABC transporter membrane-spanning permease-manganese transport protein.

Embodiment 54

The method of embodiment 44, wherein the modification is selected from one of: deletion, attenuation and reduced expression; of a streptococcal gene selected from at least one of: psaB, psaC, and homologs thereof.

Embodiment 55

The method of embodiment 44, wherein the modification enhances expression of a streptococcal gene selected from at least one of: psaR, mntE, mgtA, and homologs thereof.

Embodiment 56

The method of embodiment 44, wherein the modification is selected from one of: deletion, suppression and enhancement; of a regulatory sequence capable of altering expression of at least one streptococcal gene selected from: psaB, psaC, mntE, mgtA, and homologs thereof.

Embodiment 57

The method of embodiment 44, wherein the modification is selected from one of: deletion, attenuation and suppression; of at least one streptococcal gene selected from: sczA, czcD, copA, cupA, copY and homologs thereof; to thereby restrict intracellular levels of manganese ($Mn^{2+}$) in the bacteria.

Embodiment 58

The method of embodiment 44, wherein the modification is overexpression of at least one streptococcal gene selected from: adcA, adcAII, adcC, adcB, and homologs thereof; to thereby restrict intracellular levels of manganese ions ($Mn^{2+}$) in the bacteria.

Embodiment 59

The method of embodiment 44, wherein the attenuated or killed streptococcal bacteria were cultured with an ionophore to thereby increase cellular uptake of cations selected from at least one of: $Zn^{2+}$, $Cu^{2+}$, $Co^{2+}$, $Ni^{2+}$, $Fe^{2+}$, and $Cd^{2+}$.

Embodiment 60

The method of embodiment 59, wherein the ionophore is selected from at least one of: pyrithione, 8-hydroxyquinoline, and an analogue thereof.

Embodiment 61

The method of embodiment 44, wherein the attenuated or killed streptococcal bacteria were cultured in media comprising cations that compete with manganese ion binding sites on the bacteria.

Embodiment 62

The method of embodiment 61, wherein the cations comprise at least one of: $Zn^{2+}$, $Cu^{2+}$, $Co^{2+}$, $Ni^{2+}$, $Fe^{2+}$, and $Cd^{2+}$.

Embodiment 63

The method of embodiment 61, wherein the cations interact with a streptococcal protein selected from: MgtA riboswitch and homologs thereof: to thereby alter regulation of manganese transport genes in the bacteria.

Embodiment 64

The method of embodiment 61, wherein the cations interact with a streptococcal protein selected from: MgtA riboswitch, and homologs thereof: to thereby increase cellular uptake of the cations in the bacteria.

Embodiment 65

The method of embodiment 61, wherein the attenuated or killed streptococcal bacteria were cultured in media comprising a molar excess of the cations sufficient to inhibit PsaA protein function.

Embodiment 66

The method of embodiment 44, wherein the attenuated or killed streptococcal bacteria were cultured with at least one of a chelating agent, and an adsorption agent; to thereby reduce the availability of manganese ions to the bacteria.

Embodiment 67

The method of embodiment 66, wherein the agent is selected from at least one of: Ethylenediaminetetraacetic acid (EDTA), trans-1,2-Diaminocyclohexane-N,N,N',N'-tetraacetic acid (CyDTA), N,N,N',N'-tetrakis(2-pyridinylmethyl)-1,2-ethanediamine (TPEN), and Calprotectin.

Embodiment 68

The method of embodiment 66, wherein the attenuated or killed streptococcal bacteria were cultured in media pretreated with Chelex 100 cation chelating resin.

Embodiment 69

The method of embodiment 44, wherein the attenuated or killed streptococcal bacteria were cultured in any of: —media without manganese ions. —media depleted of manganese ions, —media with minimal manganese ions sufficient to support growth of the bacteria.

Embodiment 70

The method of embodiment 44, wherein the attenuated or killed streptococcal bacteria were cultured in media comprising an antagonist of at least one streptococcal protein selected from: PsaA, PsaB, PsaC, PsaR, MntE, and homologs thereof.

Embodiment 71

The method of embodiment 44, wherein the attenuated or killed streptococcal bacteria were cultured in media comprising an antagonist of a regulatory sequence capable of altering expression of at least one streptococcal gene selected from: psaB, psaC, mntE, mgA, and homologs thereof.

Embodiment 72

The method of embodiment 44, wherein the modification arises from at least one of: altering chromosomal DNA of the bacteria, transformation of the bacteria with a plasmid, culturing the bacteria under selective pressure, knocking down a gene of the bacteria, and introducing a transposon into DNA of the bacteria.

Embodiment 73

The method of embodiment 44, wherein the killed streptococcal bacteria were killed by at least one of: chemical treatment, thermal treatment, radiation, high hydrostatic pressure, pulsed electric field, ultrashort pulsed laser, ultrasound under pressure, and microbial inactivation.

Embodiment 74

The method of embodiment 73, wherein the chemical inactivation comprises inactivation using at least one of: a cross-linking agent, and an alkylating agent.

Embodiment 75

The method of embodiment 74, wherein the cross-linking agent is formalin.

Embodiment 76

The method of embodiment 74, wherein the alkylating agent is beta-propiolactone.

Embodiment 77

The method of embodiment 73, wherein the radiation comprises at least one of: ultraviolet, photon, proton, heavy ion, and low-energy electron irradiation.

Embodiment 78

The method of embodiment 77, wherein the photon radiation comprises gamma irradiation.

Embodiment 79

The method of embodiment 44, wherein the bacteria further comprise a defect in at least one streptococcal gene selected from: a gene encoding a DNA alkylation repair protein, a gene encoding hemolysin, a gene encoding pneumolysin, a gene encoding pneumolysin, a gene encoding autolysin, and a gene encoding DNA polymerase IV.

Embodiment 80

The method of embodiment 44, wherein the attenuated or killed streptococcal bacteria further comprise a defect in at least one streptococcal gene selected from: adcR, cibAB, hexA, hexB, ply, luxS, lyA, mutS, prtA, radC, recA, recF, recN, recO, ritR, uvrA, uvrB, uvrC, uvrD, rrgA, and homologs thereof.

Embodiment 81

The method of embodiment 44, wherein the attenuated or killed streptococcal bacteria are further modified to overexpress at least one of: PspA, PitA, PiuA, PiaA, AdcA, AdcAII, PhtA, PhtB, PhtD, PhtE, PcpA, CbpA, RrgA, RrgB, RrgC, StkP, PrtA and homologs thereof.

Embodiment 82

The method of embodiment 44, wherein the attenuated or killed streptococcal bacteria are not capable of producing a polysaccharide capsule.

Embodiment 83

The method of embodiment 44, wherein the attenuated or killed streptococcal bacteria are of a single streptococcal species or serotype.

Embodiment 84

The method of embodiment 44, wherein the attenuated or killed streptococcal bacteria comprise or consist of *Streptococcus pneumoniae* that are not psaA deletion mutants.

Embodiment 85

The method of embodiment 44, wherein the attenuated or killed streptococcal bacteria comprise at least one of: *Streptococcus agalactiae, Streptococcus bovis, Streptococcus canis, Streptococcus dysgalactiae, Streptococcus equi, Streptococcus equinus, Streptococcus equisimilis, Enterococcus faecalis, Enterococcus faecium, Streptococcus iniae, S. milleri, Streptococcus mutants, Streptococcus pneumoniae, Streptococcus pyogenes, Streptococcus salivarius, Streptococcus sanguinis, Streptococcus suis,* and *Streptococcus uberis.*

Embodiment 86

The method of embodiment 44, further comprising at least one of: an adjuvant, a pharmaceutically acceptable excipient, and a pharmaceutically acceptable carrier.

Embodiment 87

The method of embodiment 50, wherein the single species of streptococcal bacteria is *Streptococcus pneumoniae.*

Embodiment 88

The vaccine composition of embodiment 1, wherein the attenuated or killed streptococcal bacteria are further modified to overexpress at least one of: PsaR, and homologs thereof.

Embodiment 89

The vaccine composition of embodiment 88, wherein the attenuated or killed streptococcal bacteria are further modified to overexpress at least one of: PcpA, PrtA, RrgA, RrgB, RrgC and homologs thereof.

Embodiment 90

The method of embodiment 44, wherein the attenuated or killed streptococcal bacteria are further modified to overexpress at least one of: PsaR, and homologs thereof.

Embodiment 91

The method of embodiment 90, wherein the attenuated or killed streptococcal bacteria are further modified to overexpress at least one of: PcpA, PrtA, RrgA, RrgB, RrgC and homologs thereof.

Embodiment 92

The vaccine composition of embodiment 1, wherein the vaccine composition does not comprise an adjuvant.

Embodiment 93

The method of embodiment 44, wherein the vaccine composition does not comprise an adjuvant.

Embodiment 94

The vaccine composition of embodiment 1, wherein the attenuated or killed streptococcal are whole bacteria.

Embodiment 95

The method of embodiment 44, wherein the attenuated or killed streptococcal are whole bacteria.

BRIEF DESCRIPTION OF THE DRAWINGS

Preferred embodiments of the present invention will now be described, by way of non-limiting example only, with reference to the accompanying figures wherein:

FIG. 1 is a flow chart illustrating the procedure adopted to generate a strain harboring a deletion of the psaC gene in the S. pneumoniae GPN-001 strain.

FIGS. 5A and 5B provide graphs depicting the stimulation of Toll-like receptors by streptococcal bacteria according to embodiments of the present invention. These data reveal that streptococcal bacteria, whether live attenuated or killed, possessing a deletion mutation in the solute binding protein (psaA; strain GPN-002) stimulate higher TLR2 activation compared with strain GPN-001 that contains an intact psaA gene.

FIGS. 7A and 7B provide graphs showing protective immunity in mice vaccinated with streptococcal bacteria according to embodiments of the present invention. Data points indicate the survival time for each mouse (n=10-11 per group), and horizontal bars indicate the median survival time for each group. Differences in survival time were analyzed by Mann-Whitney U-test (*=P<0.05).

DEFINITIONS

Figure 2:
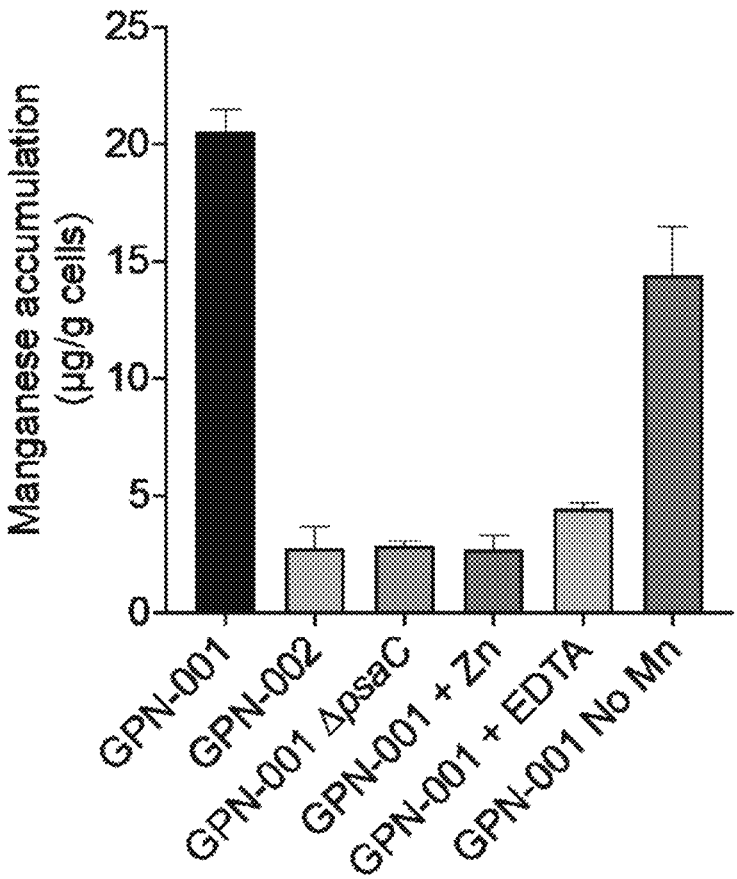
FIG. 2 depicts the manganese content of streptococcal bacteria grown with the indicated treatments or in strains possessing mutations in genes encoding components of the manganese uptake pathway. These data show that deletion mutation of the solute binding protein (psaA; strain GPN-002), or the permease protein (psaC: strain GPN-001 ΔpsaC), or growth of strain GPN-001 in the presence of zinc, EDTA or with the manganese omitted from the medium results in a reduction in cellular manganese levels, compared to the GPN-001 strain grown under the standard conditions. Data are presented as the mean manganese concentration (micrograms per gram of cell material; μg/g)±SEM from n=3 independent growth experiments.

As used in this application, the singular form "a", "an" and "the" include plural references unless the context clearly dictates otherwise. For example, the phrase "protein" also includes a plurality of proteins.

As used herein, the term "comprising" means "including." Variations of the word "comprising", such as "comprise" and "comprises," have correspondingly varied meanings. Thus, for example, a composition "comprising" streptococcal strain A may consist exclusively of gamma-irradiated streptococcal strain A or may include additional component/s (e.g. streptococcal strain B).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

The term "therapeutically effective amount" as used herein, includes within its meaning a non-toxic but sufficient amount of an agent or composition for use in the present invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation.

As used herein the term "photon-radiation" will be understood to encompass both gamma-radiation (i.e. gamma-rays) and X-radiation (i.e. X-rays). Accordingly, a "photon-irradiated" material may be one that has been exposed to gamma-radiation and which has consequently become "gamma-irradiated", one that has been exposed to X-radiation and which has consequently become "X-irradiated", or both. By way of non-limiting example only, to become photon-irradiated a material may be subjected to photon-radiation at energies of at least 0.01 MeV, at least 0.1 MeV, at least 0.5 MeV, between 0.01 MeV and 0.5 MeV, between 0.01 MeV and 1 MeV, between 0.01 MeV and 10 MeV, between 0.5 MeV and 20 MeV, between 0.5 MeV and 15 MeV, between 0.5 MeV and 10 MeV, between 0.5 MeV and 5 MeV, between 0.5 MeV and 2 MeV, or between 1 MeV and 2 MeV (e.g. 1.25 MeV).

As used herein, the term "attenuated" in the context of bacteria will be understood to mean that the bacteria are capable of establishing only non-pathogenic infection in a host to which they are administered, for a time period sufficient to induce an immune response in the host. The bacteria are not however capable of establishing long-term infection or establishing pathogenic infection that is detrimental to a non-immunocompromised host to which the attenuated bacteria are administered.

As used herein the terms "induce", "inducing", "enhance" and "enhancing" in the context of immunity or an immune response refer to an increase in immunity or an immune response above existing levels which may be absent or measurable.

As used herein, the term "subject" includes any animal of economic, social or research importance including bovine, equine, ovine, primate, avian and rodent species. Hence, a "subject" may be a mammal such as, for example, a human or a non-human mammal (e.g. a pig, cat, dog, cow, horse, or sheep). Also included within the scope of this term are laboratory animals (e.g. rodents, rabbits, and the like), birds (e.g. poultry), fish and crustaceans.

As used herein the terms "prevent", "prevention" and "preventing" in the context of a given infection and/or a disease or condition arising from the infection will be understood to mean that a subject has a reduced propensity to develop the infection, and/or disease or condition upon exposure to a pathogenic organism causative of the infection, disease or condition. The reduced propensity to develop the infection and/or disease or condition will be understood to include both a diminished propensity and a lack of any propensity.

As used herein the terms "treat" and "treating" in the context of a given infection and/or a disease or condition arising from the infection will be understood to encompass reducing the number of pathogenic organisms infecting a subject and/or reducing any symptoms of the infection and/or symptoms of a disease or condition arising from the infection.

As used herein, the terms "homolog", "homologous" and "homologs thereof" when used in connection with a reference protein will be understood to include other proteins that perform the same biological function as the reference protein. In the case where the reference protein is made by a given bacterium the other proteins may, for example, be made by another related bacterial serotype, species, genus or family member. The other proteins may share specific levels of sequence identity with the reference protein when optimally aligned such as, for example, at least about 60% identity, at least about 70%, at least about 80%, at least about 90%, or at least about 95% identity over the full length of the protein.

As used herein, the terms "homolog", "homologous" and "homologs thereof" when used in connection with a reference nucleic acid sequence will be understood to include other nucleic acid sequences that encode proteins performing the same biological function as the protein encoded by the reference nucleic acid sequence. Homologs of genes include orthologs (i.e. genes expressed in different species that evolved from common ancestral genes by speciation and encode proteins retain the same function), but do not include paralogs (i.e. genes that are related by duplication but have evolved to encode proteins with different functions).

Homologs of genes include naturally occurring alleles and artificially-created variants. The homolog may be, for example, any one or more of a bacterial homolog, a firmicute homolog, a bacilli homolog, a lactobacillales homolog, a streptococcaceae homolog, and a *streptococcus* homolog.

As used herein, a "wild-type" form of a given nucleic acid, protein or microorganism (e.g. bacteria) will be understood to encompass naturally-occurring forms of the nucleic acid, protein or microorganism and the biological functions that they are capable of.

It will be understood that use of the term "about" herein in reference to a recited numerical value includes the recited numerical value and numerical values within plus or minus ten percent of the recited value.

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

As used herein, the terms "pneumococcal surface adhesin", "pneumococcal surface antigen", and "Psa" are used interchangeably and will be understood to be a reference to the same entity. Thus, a homolog of one entity will also be a homolog of the others. Likewise, the terms "pneumococcal surface adhesin A", "pneumococcal surface antigen A", and "PsaA" are also used interchangeably and will be understood to be a reference to the same entity. Thus, a homolog of one entity will also be a homolog of the others.

Any description of prior art documents herein, or statements herein derived from or based on those documents, is not an admission that the documents or derived statements are part of the common general knowledge of the relevant art. For the purposes of description all documents referred to herein are hereby incorporated by reference in their entirety unless otherwise stated.

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

Streptococcal infections are prevalent worldwide and can cause a wide range of diseases from mild infections like the common strep throat to life-threatening conditions such as toxic shock syndrome (TSS) or meningitis. If left untreated, *streptococci* can lead to chronic autoimmune diseases such as rheumatic heart disease causing permanent damage to the heart muscle. Since antibiotics alone have not been able to control these infections, the development of effective vaccines is paramount.

Regardless, the development of vaccines to prevent streptococcal infection has been problematic in some cases due to concerns regarding autoimmune responses. When sufficiently large doses of M protein have been given to provoke type-specific antibody responses, local and systemic reactions have been frequent. Another approach to immunization, namely the stimulation of antibodies directed to lipoteichoic acid (the adherence moiety of *streptococci*), is limited by the poor immunogenicity of this constituent unless complexed to a protein molecule. Although vaccination with capsular polysaccharides has shown some efficacy in preventing *S. pneumoniae* infection in otherwise healthy adults, the benefits of vaccination in individuals with increased susceptibility due to age or other chronic disease are limited and these subjects are least likely to respond with adequate production of antibody. Additionally, despite their efficacy against disease caused by targeted vaccine serotypes, serotype replacement often reduces the net effect of vaccination. The emergence of non-vaccine serotypes upon the implementation of pneumococcal conjugate vaccines thus raises a problem.

The present invention provides streptococcal vaccines capable of inducing enhanced levels of immunity compared to at least some existing streptococcal vaccines. Additionally or alternatively, the streptococcal vaccines described herein may induce immunity against a broader spectrum of streptococcal strains compared to at least some Streptococcal vaccines existing in the art. The present invention also contemplates methods for producing the Streptococcal vaccines described, as well as methods for their use in inhibiting and/or preventing infection by streptococcal bacteria in subjects to which the vaccines are administered.

Streptococcal Vaccine Preparations

Streptococcal Strains

Vaccines of the present invention are based on attenuated or killed streptococcal bacteria (e.g. whole killed streptococcal bacteria), and/or components thereof. The components thereof are typically immunogenic components such as, for example, antigenic proteins or part/s of antigenic proteins normally exposed to the external host environment, cell wall bacterial antigens (polysaccharides), and the like.

The streptococcal bacteria may be pathogenic bacteria capable of establishing a detrimental infection in a host organism. Vaccines of the invention may comprise combinations of different attenuated and/or different killed streptococcal bacteria and/or components thereof, including, for example, combinations of different streptococcal species, and/or combinations of different streptococcal serotypes within the same streptococcal species.

The streptococcal bacteria may, for example, be alpha-, beta-, or gamma-haemolytic *streptococci*, as classified according to well-characterised haemolytic properties or lack thereof in the case of gamma-haemolytic streptococcal bacteria.

Non-limiting examples of suitable alpha-haemolytic streptococcal bacteria include *Streptococcus pneumoniae* and *viridans streptococci* (e.g. *S. mutans. S. sanguinis, S. mitis, S. oralis, S. sobrinus, S. milleri*). Also within the scope of the present invention are individual serotypes of these streptococcal species.

Non-limiting examples of suitable beta-haemolytic streptococcal bacteria include those classified under the Lancefield grouping (Groups A-H, L, N and R/S) based on the carbohydrate composition of cell wall bacterial antigens (polysaccharides). For example, the beta-haemolytic bacteria may include any one or more of *S. pyogenes* (Group A), *S. agalactiae* (Group B), *S. equisimilis* (Group C), *S. equi* (Group C), *S. zooepidemicus* (Group C), *S. dysgalactiae* (Group C), *Enterococcus faecalis* (Group D), *S. bovis* (Group D), *S. milleri* (Group E). *S. mutans* (Group E), *S. anginosus* (Group F), *S. canis* (Group G), *S. dysgalactiae* (Group G), *S. sanguis* (Group H), *S. dysgalactiae* (Group L), *Lactococcus lactis* (Group N), and *S. suis* (Group R/S). Also within the scope of the present invention are individual serotypes of these streptococcal species.

In some embodiments, vaccines of the present invention comprise one or more serotypes of *Streptococcus pneumoniae*. Accordingly, the vaccines may comprise any one of more of *S. pneumoniae* serotypes 1, 2, 3, 4, 5, 6A, 6B, 6C, 6D, 7A, 7B, 7C, 7F, 8, 9A, 9L, 9N, 9V, 10A 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 27, 28A 28F, 29, 31, 32A, 32F, 33A, 33B, 33C, 33D, 33F, 34, 35A, 35B, 35C, 35F, 36, 37, 38, 39, 40, 41A, 41F, 42, 43, 44, 45, 46, 47A, 47F, and/or 48.

In some embodiments, the vaccines comprise any one or more of *S. pneumoniae* serotypes 1, 2, 3, 4, 5, 6A, 6B, 7F, 8, 9N, 9V, 10A, 11A, 12F, 14, 15B, 17F, 18C, 19A 19F, 20, 22F, 23F, and 33F.

Streptococcal Mutants: Reduced Intracellular Manganese

As noted above, vaccines of the present invention may be based on attenuated or killed streptococcal bacteria (e.g. whole killed streptococcal bacteria), and/or components thereof.

The components thereof are typically immunogenic components such as, for example, antigenic proteins or part/s of antigenic proteins normally exposed to the external host environment, cell wall bacterial antigens (polysaccharides), and the like.

The streptococcal bacteria may be mutant streptococcal bacteria, modified to alter one or more characteristics that directly or indirectly reduce their intracellular levels of manganese ions ($Mn^{2+}$). The mutant streptococcal bacteria may be generated from wild-type recombinant forms of streptococcal bacteria by any suitable means such as, for example, genetic manipulation, applying artificial selection pressure/s, and the like.

Techniques for the genetic manipulation of bacteria are well known to those of ordinary skill in the art (see, for example, Vennison "*Laboratory Manual for Genetic Engineering*", PHI Learning Pvt. Ltd., 2010; Zyskind and Bernstein, "*Recombinant DNA Laboratory Manual*", Elsevier, 2014: Bose, "*Genetic Manipulation of Staphylococci*" in "Methods in Molecular Biology", Springer Protocols, volume 1106, pages 101-111, 2014; Hakenbeck and Chhatwal, "*Molecular Biology of Streptococci*", Horizon Scientific Press, 2007; Morona et al., "*The effect that mutations in the conserved capsular polysaccharide biosynthesis genes cpsA, cpsB and cpsD have on virulence of Streptococcus pneumoniae*", J. Infect. Dis, 189: 1905-1913, 2004; Morona et al., "*Mutational analysis of the carboxy-terminal [YGX]₄ repeat domain of CpsD, an autophosphorylating tyrosine kinase required for capsule biosynthesis in Streptococcus pneumonia*", J. Bacteriol, 185: 3009-3019, 2003: McAllister et al., "*Molecular analysis of the psa permease complex of Streptococcus pneumoniae*", Mol. Microbiol, 53:889-901, 2004; Mahdi et al., "*Identification of a novel pneumococcal vaccine antigen preferentially expressed during meningitis in mice*", J. Clin. Invest, 122:2208-2220, 2012.

Non-limiting examples of mutant streptococcal bacteria contemplated include those with one or more mutation/s which restrict intracellular levels of manganese ions ($Mn^{2+}$), for example, by enhancing efflux of manganese ions and/or by inhibiting influx of manganese ions. Any suitable modification or combination of modifications that can be made to the streptococcal bacteria to reduce intracellular manganese are included within the scope of the present invention.

By way of non-limiting example, the streptococcal bacteria may be modified to delete or to introduce a defect into a streptococcal manganese transporter protein or a component thereof, a gene encoding a bacterial manganese transporter or a component thereof, and/or a regulatory sequence that positively regulates expression of a gene encoding a bacterial manganese transporter or a component thereof. Non-limiting examples of suitable modifications include the introduction of mutations into the protein, gene, regulatory sequence and/or component/s thereof, such as for example, any one or more of substitution/s, deletion/s, insertion/s, a stop codon/s, frameshift mutation/s, and the like.

In some embodiments, the streptococcal manganese transporter protein is a pneumococcal surface antigen protein (also known in the art as a pneumococcal surface adhesin protein), or a component thereof (e.g. any one or more of *Streptococcus pneumoniae* PsaA, PsaB, PsaC). In other embodiments, the streptococcal manganese transporter protein is a homolog of a pneumococcal surface antigen protein or a component thereof, or a homolog of any one or more of PsaA, PsaB, PsaC.

As known to those skilled in the art, PsaA is the solute binding protein of the manganese-specific ATP-binding cassette (ABC) transporter, and is responsible for delivery of manganese to the other transporter component (PsaC). PsaB protein is the ATP binding protein of this transporter and is responsible for ATP hydrolysis to power the transport of manganese, while PsaC is the transporter permease (membrane component) responsible for translocation of manganese into the streptococcal cell. Accordingly, the modification and/or deletion of any one or more of PsaA, PsaB and/or PsaC or homologs thereof can be used to inhibit manganese influx thereby reducing intracellular levels of the ion.

In other embodiments, the streptococcal manganese transporter protein is not a pneumococcal surface antigen protein, or a component thereof (e.g. is not any one or more of *Streptococcus pneumoniae* PsaA, PsaB, PsaC). In other embodiments, the streptococcal manganese transporter protein is not a homolog of a pneumococcal surface antigen protein or a component thereof, or not a homolog any one or more of PsaA, PsaB, PsaC.

By way of non-limiting example: homologs of *Streptococcus pneumoniae* PsaA include, but are not limited to, *Streptococcus sanguinis* SsaB, *Streptococcus gordonii* Sgo, *Streptococcus parasanguinis* FimA, *Streptococcus agalactiae* MtsA, *Streptococcus iniae* MtsA, *Streptococcus pyogenes* MtsA, *Streptococcus uberis* MtuA, and *Streptococcus mutans* SloC; homologs of *Streptococcus pneumoniae* PsaB include, but are not limited to: *Streptococcus sanguinis* SsaA, *Streptococcus gordonii* ScaC, *Streptococcus* parasanguinis FimC, *Streptococcus iniae* MtsB, *Streptococcus mutans* SloA, *Streptococcus pyogenes* MtsB, *Streptococcus uberis* MtuB, *Streptococcus agalactiae* MtsB; and homologs of *Streptococcus pneumoniae* PsaC include, but are not limited to: *Streptococcus sanguinis* SsaC, *Streptococcus gordonii* ScaB, *Streptococcus parasanguinis* FimB, *Streptococcus iniae* MtsC, *Streptococcus mutans* SloB, *Streptococcus pyogenes* MtsC, *Streptococcus uberis* MtuC, *Streptococcus agalactiae* MtsC.

As used herein a homolog of a protein refers to a protein within a group of proteins that perform the same biological function, and which are expressed by homologous genes. Homologous genes are genes which encode proteins with the same or similar biological function to the protein encoded by the second gene. Homologous genes and nucleic acid sequences can be present in the same or a different organism. Homologous genes include orthologs (i.e. genes expressed in different species that evolved from common ancestral genes by speciation and encode proteins retain the same function), but do not include paralogs (i.e. genes that are related by duplication but have evolved to encode proteins with different functions). Homologous genes include naturally occurring alleles and artificially-created variants. Degeneracy of the genetic code provides the possibility to substitute at least one nucleotide of the protein-encoding sequence of a gene or coding sequence with a different base without altering the amino acid sequence of the polypeptide produced from the gene. When optimally aligned, homologous proteins and nucleotide sequences (e.g. genes) of the present invention may, for example, have at least about 20%, 30%, 40%, 50%, 60%, 70%, 75%, 80%, 85%, 90%, 95%, 96%, 97%, 98% or 99% sequence identity over the full length of the reference gene or protein. In some embodiments, a homologous nucleotides sequences (e.g. genes) or homologous protein sequence of the present invention has at least about 20%, 30%, 40%, 50%, 600%, 70%, 75%, 80%, 85%, 90%, 95%, 96%, 97%, 98% or 99% sequence identity to a reference consensus nucleotide or protein sequence over the full length of the reference sequence. A homologous nucleic acid sequence, gene, or protein described herein may be, for example, a homologous nucleic acid sequence, gene, or protein from other bacteria, from other firmicutes, from other bacilli, from other lactobacillales, from there streptococcaceae, and/or from other *streptococci*.

Genes/nucleic acid sequences and proteins that are homologs of reference sequences can be identified by comparison of homologous amino acid or nucleotide sequence (e.g. manually or using a computer-based tool employing known homology-based search algorithms such as FASTA, BLAST, and Smith-Waterman). A local sequence alignment program (e.g. BLAST), can be used to find similar sequences by searching in a database of sequences, and the summary Expectation value (E-value) can be used to measure the sequence base similarity. As a given sequence hit with the best E-value for a particular organism may not necessarily be an ortholog (i.e. have the same function/encode a protein having the same function), or be the only ortholog, a reciprocal query may be used to filter hit sequences with significant E-values for ortholog identification. The reciprocal query may entail searches of the significant hits against a database of sequences from the base organism that are similar to the sequence of the query sequence. A hit can be identified as an ortholog, when the reciprocal query's best hit is the query sequence itself or a protein encoded by a duplicated gene after speciation.

As used herein. "% sequence identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "% sequence identity" is the identity fraction times 100. Such optimal alignment is understood to be deemed as local alignment of DNA sequences. For protein alignment, a local alignment of protein sequences should allow introduction of gaps to achieve optimal alignment. Percent sequence identity is calculated over the aligned length not including the gaps introduced by the alignment per se.

In other embodiments, the streptococcal bacteria may be modified to overexpress a streptococcal manganese transporter protein or a component thereof, a gene encoding a bacterial manganese transporter or a component thereof, and/or a regulatory sequence that negatively regulates expression of a gene encoding a bacterial manganese transporter or a component thereof. In this context, "overexpress" will be understood to mean a level of expression that is increased compared to expression of the same gene or protein in a wild-type form of the same streptococcal bacterium, under the same biological conditions. Non-limiting examples of suitable streptococcal manganese transporters in this category include the *Streptococcus pneumoniae* MntE manganese efflux transporter, MgtA and homologs thereof. As known to those of skill in the art, MntE is a major manganese export protein (a Cation Diffusion Facilitator family protein) while MgtA is a P-type ATPase protein with a function in manganese efflux. Both export manganese from the cytoplasm and hence these proteins and their homologs can be overexpressed in streptococcal mutants of the present invention to reduce levels of intracellular manganese ions.

As an additional or alternative approach to any of the above, the streptococcal bacteria may be modified to overexpress a regulator (repressor) of one or more gene/s encoding the *Streptococcus pneumoniae* manganese ABC transporter (psaA, psaB, psaC) or homologs of such gene/s. By way of non-limiting example, overexpression of the psaR regulator/repressor or homologs thereof may be used to increase PsaR-DNA binding and repression of the psaA, psaB and/or psaC genes (or their homologs). Reduced transcription of these genes may reduce manganese ion uptake from the external environment providing reduced levels of intracellular manganese ions. However, overexpression of PsaR may also downregulate the expression of other genes including, for example, pcpA, prtA and/or rrgA, which may encode immunogenic proteins. In some embodiments, if overexpressing PsaR or a homolog thereof, any genes consequently downregulated may have their expression levels re-established or raised by use of, for example, a constitutive promoter.

As an additional or alternative approach to any of the above, the streptococcal bacteria may be modified to alter the activity of transcriptional activator/s of gene/s encoding manganese transporters. As known to those of skill in the art, the mg/A riboswitch is a cis-acting small RNA (riboswitch) which acts as a regulatory element to control the expression of the manganese efflux protein mgtA. It acts as a manganese-specific sensor that activates the transcription of mgtA, whereby binding of manganese to the RNA aptamer destabilises the terminator hairpin and permits transcription of full-length mgtA mRNA transcript. By way of non-limiting example, alteration of the sequence of the mgtA riboswitch or a homolog thereof such that the RNA sequence no longer has structural features that form the hairpin may be used to increase transcription of mgtA or homologs thereof. This overexpression may induce manganese depletion by way of increasing its efflux from the bacterial cells.

As an additional or alternative approach to any of the above, a streptococcal zinc transporter protein may be modified (e.g. overexpressed) to influence intracellular levels of zinc ions ($Zn^{2+}$), which may in turn bind to PsaR and thereby reduce the expression of genes encoding manganese transporters (e.g. psaA, psaB and psaC). Non-limiting examples of suitable streptococcal zinc transporters for this purpose include *Streptococcus pneumoniae* AdcAII, *Streptococcus pneumoniae* AdcA, *Streptococcus pneumoniae* AdcB, *Streptococcus pneumoniae* AdcC and *Streptococcus pneumoniae* CzcD, *Streptococcus agalactiae* Lmb, *Streptococcus pyogenes* AdcA, *Streptococcus pyogenes* Lmb, and homologs thereof.

As an additional or alternative approach to any of the above, the streptococcal bacteria may be modified to express one or more proteins which are upregulated as a result of reduced intracellular manganese ion levels. Non-limiting examples of such proteins include; PcpA. PrtA, RrgA, RrgB and RrgC. The skilled addressee will recognise that while these proteins can be upregulated as an outcome of reduced intracellular manganese ion levels, alternative approaches may be adopted to achieve the same outcomes. For example, the streptococcal bacteria may be genetically engineered to overexpress one or more of the proteins using expression vectors and the like, and/or other art-known approaches.

Cell Culture Methodology to Reduce Intracellular Levels of Manganese Ions

As described herein, vaccines of the present invention may be based on attenuated or killed streptococcal bacteria (e.g. whole killed streptococcal bacteria), and/or components thereof. The components thereof are typically immunogenic components such as, for example, antigenic proteins or part/s of antigenic proteins normally exposed to the external host environment, cell wall bacterial antigens (polysaccharides), and the like.

The streptococcal bacteria described herein, including both wild-type and mutant forms, may be cultured in a manner that restricts levels of intracellular manganese ($Mn^{2+}$). This may be in addition to, or independent of, introducing mutation/s into the bacteria to reduce their intracellular levels of manganese ions ($Mn^{2+}$).

As is well known to those of skill in the art, manganese ions are required for streptococcal growth and function. The widespread availability of standard culture media and protocols means that the optimal levels of such ions to facilitate the growth of wild-type streptococcal bacteria in culture is well established, and can be readily determined by those of ordinary skill in the art by simple trial and error.

In some embodiments, the streptococcal bacteria described herein may be cultured under conditions that reduce the availability of manganese ions to the bacteria under culture, and consequently facilitate reduced levels of intracellular manganese within the bacteria.

By way of non-limiting example, the streptococcal bacteria may be cultured in media (e.g. standard) depleted of manganese ions to levels below those known or established to be optimal for their growth. In some embodiments, the media may be pre-treated and/or treated during culturing of the bacteria with agent/s (e.g. absorption agent/s and/or a chelating agent/s) capable of sequestering manganese ions thus reducing their availability to the bacteria. For example, a chelating resin (e.g. Chelex 100 cation chelating resin) may be used to sequester and remove manganese ions from the media prior to culturing the bacteria and/or during the culture (e.g. at intervals) of the bacteria. Additionally or alternatively, the media may be supplemented with one or more agent/s capable of chelating manganese ions such as, for example, any one or more of Ethylenediaminetetraacetic acid (EDTA), trans-1,2-Diaminocyclohexane-N,N,N',N'-tetraacetic acid (CyDTA). N,N,N',N'-tetrakis(2-pyridinylmethyl)-1,2-ethanediamine (TPEN), and Calprotectin. For those agents that chelate metal ions in addition to $Mn^{2+}$, the media may be appropriately re-supplemented with those other ions to enable cell growth. The skilled addressee will be aware of appropriate concentrations to utilise.

Additionally or alternatively, the streptococcal bacteria may be cultured in media comprising an excess (e.g. a molar excess) of cations that compete with manganese ion binding sites in and/or on the bacteria (e.g. streptococcal PsaA and/or homologs thereof). The competing ions may include other cations such as, for example, any one or more of $Zn^{2+}$, $Cu^{2+}$, $Co^{2+}$, $Ni^{2+}$, $Fe^{2+}$ and $Cd^{2+}$. By way of non-limiting example, binding of the cations to PsaA or homologs thereof may lock the protein in its closed conformation, preventing the uptake of manganese and reducing intracellular levels of the ion.

The skilled addressee will acknowledge that any number of other alternative mean/s may be used to reduce or remove manganese ions from media used to culture the streptococcal bacteria described herein, all of which are contemplated.

Streptococcal mutants: Further Exemplary Alterations

By way of non-limiting example only, mutant streptococcal strains of the present invention may comprise various other alteration/s in addition to, or independent of, measures that restrict intracellular levels of manganese ions in the strains (e.g. by mutation/s and/or by culture under conditions that reduce intracellular manganese levels). Non-limiting examples of these alteration/s follow below.

In some embodiments, the alteration/s include any which disrupt or remove the streptococcal capsule locus (cps). For example, any one or more of the S. pneumoniae cpsA, cpsB, cpsC, cpsD and/or cpsE genes, or homologous genes in other streptococcal species, may be modified in order to prevent, disrupt or modify capsule production (e.g. by site-directed mutagenesis and the like). Alternatively, the streptococcal mutants may have spontaneous mutations in these or other genes resulting in naturally-occurring non-encapsulated streptococcal bacteria. The streptococcal mutants may lack all or at least a portion of the capsule locus. In some embodiments, the streptococcal mutants lacking a capsule are Streptococcus pneumoniae strain Rx1, or Rx1 derivatives.

Additionally or alternatively, the alteration/s may include any which increase or reduce or prevent the production or activity of other target proteins. By way of non-limiting example only, the genetic alteration may exist in: one or more genes encoding a choline-binding protein; one or more genes encoding an autolysin (e.g. S. pneumoniae lytA, lytB, lytC or homologous genes in other streptococcal bacteria): one or more genes that confer a nutrient/cofactor requirement for growth; one or more genes encoding a protective antigen (e.g. S. pneumoniae pspA or homologous genes in other streptococcal bacteria); and/or one or more genes encoding virulence determinants or regulators (e.g. S. pneumoniae codY, comC, comD, cps2A, csp4A, glpO, mgrA, nanA, nanB, pavA, pcpA, phtA, phtB, phtD, phtE, piuA, piaA, ply, prA, psrP, rrgA, rrgB, spxB, and homologs of these genes in other streptococcal bacteria).

Additionally or alternatively, the alteration/s may include any which result in an auxotroph with reduced pathogenicity and/or growth in vivo. By way of non-limiting example only, the genetic alteration may exist in one or more genes encoding a thymidylate synthase.

Additionally or alternatively, the alteration/s may comprise the inclusion of one or more (external) genes from: a streptococcal bacterium that is of the same species but a different serotype; a streptococcal bacterium that is from a different species; a non-streptococcal bacterium; or a human or a non-human mammal (e.g. a pig, cat, dog, cow, horse, or sheep): a laboratory animal (e.g. a rodent or rabbit); a bird: and/or a subject to which the recombinant streptococcal bacteria are to be administered. In some embodiments, the external gene or genes disrupt or otherwise inactivate one or more endogenous gene or genes. In other embodiments, the external gene or genes do not disrupt or inactivate any endogenous gene. By way of non-limiting example only, the external gene or genes may encode proteins that induce or enhance an immune response in a subject to which the streptococcal mutants are administered. The immune response may be innate, adaptive, or both. In some embodiments, the external gene or genes encode an immunomodulator (e.g. a cytokine, chemokine, antibody, fusion protein, peptide, protein, and/or hormone). In other embodiments, the external gene or genes may comprise an antigen from another different family of bacteria (e.g. a Mycoplasma pneumoniae antigen, a Haemophilus influenzae antigen, a Chlamydophila pneumoniae antigen, a Moraxella catarrhalis antigen, a Staphylococcus aureus antigen), a viral antigen (e.g. an adenovirus antigen, a coronavirus antigen, an influenza virus antigen, a parainfluenza virus antigen, a metapneumovirus antigen, a rhinovirus antigen, a respiratory syncytial virus antigen, an HIV antigen, a hepatitis virus antigen, or a herpes virus antigen, a measles virus antigen, a mumps virus antigen, a papillomavirus virus antigen, a rubella virus antigen, a Varicella Zoster virus antigen), a fungal/yeast antigen, a helminthic antigen, and/or a protozoan antigen.

Additionally or alternatively, the alteration/s may comprise those which cause the bacteria to overexpress one or more target gene/s, for example, to induce or enhance an immune response in a subject against streptococcal strains that are parental to the streptococcal mutants administered and/or against the streptococcal mutants themselves. By way of non-limiting example only, the genetic alteration may increase the production of one or more genes in the streptococcal mutants encoding a protein capable of activating the complement system (e.g. *S. pneumoniae* cbpA, pspA, ply, or homologs of these genes in other streptococcal bacteria).

Additionally or alternatively, the alteration/s may comprise those which cause defective DNA repair capacity. In some embodiments, the streptococcal mutants comprise a genetic alteration that disrupts or inactivates expression of one or more genes encoding a protein in a mismatch repair system (e.g. *S. pneumoniae* hex locus or homologs of this locus in other streptococcal bacteria).

Additionally or alternatively, the alteration/s may comprise those which disrupt or inactivate expression of one or more genes encoding a DNA alkylation repair protein (e.g. *S. pneumoniae* DNA polymerase 4, hexA, hexB, mutS, radC, recA, recF, recN, recO, uvrA, uvrB, uvrC, uvrD or homologs of these genes in other streptococcal bacteria).

Additionally or alternatively, the alteration/s may comprise those which facilitate production of a double-stranded RNA (dsRNA). The dsRNA may be mRNA or tRNA. Without limitation, the length of the dsRNA may be more than 10, more than 15, more than 20, more than 25, more than 30, more than 35, more than 40, more than 45, more than 50, more than 55, more than, more than 65 or more than 70 base pairs in length. Additionally or alternatively, the length of the dsRNA may be: between about 10 and about 70 base pairs (bp): between about 10 and about 50 base pairs (bp); between about 10 and about 30 base pairs (bp); between about 20 and about 70 base pairs (bp); between about 20 and about 60 base pairs (bp); between about 20 and about 50 base pairs (bp): between about 20 and about 40 base pairs (bp): between about 20 and about 30 base pairs (bp): between about 30 and about 70 base pairs (bp): between about 40 and about 70 base pairs (bp): between about 50 and about 70 base pairs (bp); between about 60 and about 70 base pairs (bp); between about 30 and about 60 base pairs (bp); between about 30 and about 50 base pairs (bp); or between about 30 and about 40 base pairs (bp): in length. In some embodiments, the dsRNA is a component of a larger RNA molecule that is otherwise single-stranded. The larger RNA molecule may comprise multiple dsRNA components. The dsRNA may be an internal component or an end component of the larger RNA molecule. In some embodiments, the dsRNA may comprise a termination stem-loop sequence. The dsRNA may arise from a region of self-complementarity within the larger RNA molecule. Coding region(s)/exon(s) within a given gene of a streptococcal derivative can be engineered to include one or more region(s) of self-complementarity and thereby produce a dsRNA portion when transcribed. The dsRNA may be capable of recognition by Toll-like receptor (TLR) proteins expressed by cells in a subject to which the streptococcal mutants are administered. The TLR proteins may be located in the endoplasmic reticulum and/or endosomal compartment of the cells. The TLR proteins may be Toll-like receptor 3 (TLR3) proteins. Without limitation, the cells may be any one or more of B lymphocytes, T lymphocytes, natural killer cells and/or dendritic cells. Recognition of the dsRNA by the TLR3 protein may induce an immune response in the subject. The immune response may be an innate immune response. The immune response may be an interferon type-1 response and/or comprise the release of inflammatory cytokines.

Additionally or alternatively, the alteration/s may comprise generating an Rx1 strain.

The autolysin gene (lvtA) gene may be deleted or rendered non-functional in the Rx1 derivative strain. Additionally or alternatively, the pneumolysin gene (ply) may be deleted or rendered non-functional in the Rx1 derivative strain. For example, the ply gene may be replaced with another gene such as one encoding a toxoid version of ply. Inactivation and/or Attenuation of Streptococcal Bacteria Vaccines of the present invention are based on attenuated or killed streptococcal bacteria (e.g. whole killed streptococcal bacteria), and/or components thereof.

Inactivation of the streptococcal bacteria described herein can be achieved, for example, by use of any one or more of following methods: chemical inactivation exemplified by use of cross-linking agents such as formalin or alkylating agents such as beta-propiolactone, thermal (heat) treatment, radiation as exemplified by ultraviolet, photon, proton, heavy ion or low-energy electron irradiation, high hydrostatic pressure, pulsed electric field, ultrashort pulsed laser and ultra sound under pressure. Preferred methods of streptococcal bacteria inactivation include those which minimise the removal and/or denaturation of cell wall-associated surface protein antigens.

Non-limiting examples of suitable techniques for the bacterial inactivation and/or attenuation are disclosed in: Levinson et al. (1944) Production of potent inactivated vaccines with ultraviolet irradiation. JAMA 125, 532: Hartman F W and Lo Grippo G A (1957) Beta-propiolactone in sterilization of vaccines, tissue grafts and plasma. JAMA, 164, 258-260: Manas P and Pagan R (2005) Microbial inactivation by new methods of food preservation. Delrue I et al. (2012) Inactivated virus vaccines from chemistry to prophylaxis: merits, risks and challenges. Expert Rev. Vaccines 11, 695-719; Park J C and Jung M H (2015) Study of the effects of high-energy proton beams on *Escherichia coli*. J. Korean Physical Soc. 67, 1454-1458; J. Appl. Microbiology, 98, 1387-1399: Babb R et al. (2016) Intranasal vaccination with gamma-irradiated *Streptococcus pneumoniae* whole-cell vaccine provides serotype independent protection mediated by B-cells and innate IL-17 responses. Clin. Sci. 130, 697-710; Fertey J et al. (2016) Pathogens inactivated by low-energy-electron irradiation maintain antigenic properties and induce protective immune responses. Viruses 8, 319 doi:10.3390/v8110319: Sabbaghi A et al. (2019) Inactivation methods for whole influenza vaccine production. Rev. Medical Virology, 29 (6) e2074)).

In some embodiments, the streptococcal bacteria are inactivated by exposure to photon-radiation. As noted above, the term "photon-radiation" will be understood to encompass both gamma-radiation (i.e. gamma-rays) and X-radiation (i.e. X-rays). Accordingly, "photon-irradiated" streptococcal bacteria may be "gamma-irradiated" by way of exposure to gamma-radiation (i.e. gamma-rays), "X-irradiated" by way of exposure to X-radiation (i.e. X-rays), or both. By way of non-limiting example only, to become photon-irradiated a material may be subjected to photon-radiation at energies of at least 0.01 MeV, at least 0.1 MeV, at least 0.5 MeV, between 0.01 MeV and 0.5 MeV, between 0.01 MeV and 1 MeV, between 0.01 MeV and 10 MeV, between 0.5 MeV and 20 MeV, between 0.5 MeV and 15 MeV, between 0.5 MeV and 10 MeV, between 0.5 MeV and 5 MeV, between 0.5 MeV and 2 MeV, or between 1 MeV and 2 MeV (e.g. 1.25 MeV).

By way of non-limiting example, gamma-irradiation of the streptococcal bacteria may be performed using commercially available devices, for example, a Gammacell irradiator manufactured by Atomic Energy of Canada Ltd., Canada (e.g. Gammacell 40 Irradiator. Gammacell 220 Irradiator, Gammacell 1000 irradiator, Gammacell 3000 irradiator), a gamma-irradiator manufactured by J. L. Shepherd and Associates (San Fernando, California, USA), or a Nordion Gamma Cell-1000 irradiator manufactured by Nordion Inc. (Kanata, Ontario, Canada). Other suitable devices are described, for example, in U.S. Pat. Nos. 3,557,370 and 3,567,938. Additionally or alternatively, streptococcal bacteria in vaccines of the invention may be X-irradiated. Any suitable source of X-radiation may be used. Suitable sources of X-radiation include, but are not limited to, the eXelis® sterilization X-ray machine manufactured by IBA Industrial (Louvain-la-Neuve, Belgium). Other suitable devices include for example, the RS2400® and RS3400® manufactured by Rad Source Technologies Inc. (Suwanee, Georgia, USA). In one embodiment, preparations of streptococcal bacteria are maintained in a frozen and/or lyophilised state w % bile being exposed to photon-radiation (e.g. gamma-radiation and/or X-radiation). This may facilitate the preservation of biological integrity and avoid unnecessary damage of antigens thereby enhancing the immunogenicity of photon-irradiated bacterial preparations, and in particular, their ability to elicit cross-reactive/cross-protective immunity against, for example, heterologous strains.

Formulations

The streptococcal bacteria and component/s thereof described herein may be incorporated into pharmaceutical compositions. The compositions can stimulate an immune response against pathogenic organisms capable of establishing infection in a host that may culminate in a disease or condition. Accordingly, the compositions may be vaccines, including preventative vaccines (i.e. vaccines administered for the purpose of preventing infections and/or diseases/conditions) and therapeutic vaccines (i.e. vaccines administered for the purpose of treating infections and/or diseases/conditions). A vaccine of the present invention may therefore be administered to a recipient for prophylactic, ameliorative, palliative, or therapeutic purposes. The pharmaceutical compositions may be vaccines.

The vaccines may be prepared using methods known to those of ordinary skill in the art. Non-limiting examples of suitable methods are described in Gennaro et al. (Eds), (1990), "*Remington's Pharmaceutical Sciences*", Mack Publishing Co., Easton, Pennsylvania, USA, and methods for vaccine preparation are generally described in Voller et al., (1978), "*New Trends and Developments in Vaccines*", University Park Press, Baltimore, Maryland, USA.

The vaccines may comprise a pharmaceutically acceptable carrier, excipient, diluent and/or adjuvant. "Pharmaceutically acceptable" carriers, excipients, diluents and/or adjuvants as contemplated herein are substances which do not produce adverse reaction(s) when administered to a particular recipient such as a human or non-human animal. Pharmaceutically acceptable carriers, excipients, diluents and adjuvants are generally also compatible with other ingredients of the vaccine. Non-limiting examples of suitable excipients, diluents, and carriers can be found in the "*Handbook of Pharmaceutical Excipients*" 4th Edition, (2003) Rowe et al. (Eds), The Pharmaceutical Press, London, American Pharmaceutical Association, Washington.

Non-limiting examples of pharmaceutically acceptable carriers, excipients or diluents include demineralised or distilled water; saline solution; vegetable based oils such as peanut oil, safflower oil, olive oil, cottonseed oil, maize oil, sesame oils, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose: lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin: fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Vaccines of the present invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, intradermal, subcutaneous, intramuscular or intravenous injection.

For preparation of the vaccines as injectable solutions or suspensions, non-toxic parenterally acceptable diluents or carriers may be used such as Ringer's solution, isotonic saline, phosphate buffered saline, ethanol and 1,2 propylene glycol. Formulations suitable for topical administration include liquid or semi-liquid preparations suitable for penetration through the skin to the site of where treatment is required, such as liniments, lotions, creams, ointments or pastes, and drops suitable for administration to the eye, ear or nose. When formulated as drops, the vaccines may comprise sterile aqueous or oily solutions or suspensions. These may be prepared by dissolving the active ingredient in an aqueous solution of a bactericidal and/or fungicidal agent and/or any other suitable preservative, and optionally including a surface-active agent. The resulting solution may then be clarified by filtration, transferred to a suitable container and sterilised. For example, sterilisation may be achieved by filtration followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol. When formulated as lotions, the vaccines include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil. When formulated as creams, ointments or pastes, the vaccines may be semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap: a mucilage; an oil of natural origin such as almond, corn. arachis, castor or olive oil: wool fat or its derivatives, or a fatty acid such as stearic or oleic acid together with an alcohol such as propylene glycol or macrogols.

The vaccines may include any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The vaccines may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolizable lipid capable of forming liposomes can be used. The vaccines in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p, 33 et seq.

Adjuvants

Adjuvant(s) may be included in vaccines of the present invention. In general, adjuvant activity in the context of the vaccines include, but is not limited to, the ability to enhance the immune response (quantitatively or qualitatively) induced by immunogenic components in the vaccine. This may reduce the dose or level of the immunogenic components required to produce an immune response and/or reduce the number or the frequency of immunizations required to produce the desired immune response.

Preferably, an adjuvant will enhance the immune response induced and/or enhanced by component(s) of the vaccine thereby improving protective efficacy. Preferably, the adjuvant will enable the induction of protective immunity utilising a lower dose of other active component(s).

Non-limiting examples of adjuvants suitable for inclusion in vaccines of the invention and methods for their preparation are described in "*Vaccine Adjuvants: Preparation Methods and Research Protocols* (*Methods in Molecular Medicine*)", (2000). O'Hagan (Ed), Humana Press Inc. Any suitable adjuvant may be included in a vaccine of the invention.

Specific examples of such adjuvants include, but are not limited to, aluminum hydroxide; polypeptide adjuvants including interferons, interleukins, and other cytokines; AMPHIGEN, oil-in-water and water-in-oil emulsions; and saponins such as QuilA.

For example, an aluminum-based adjuvant may be utilized. Suitable aluminum-based adjuvants include, but are not limited to, potassium aluminum sulfate, aluminum hydroxide, aluminum phosphate and combinations thereof. Other specific examples of aluminum-based adjuvants that may be utilized are described in European Patent No. 1216053 and U.S. Pat. No. 6,372,223.

Oil in water emulsions may be utilized as adjuvants in vaccines of the invention. Oil in water emulsions are well known in the art. In general, the oil in water emulsion will comprise a metabolizable oil, for example, a fish oil, a vegetable oil, or a synthetic oil. Examples of suitable oil in water emulsions include those described in European Patent No. 0399843, U.S. Pat. No. 7,029,678 and PCT Publication No. WO 2007/006939. The oil in water emulsion may be utilized in combination with other adjuvants and/or immunostimulants.

Non-limiting examples of other suitable adjuvants include immunostimulants such as granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP), Toll-like receptor (TLR) agonists (e.g. TLR-2, TLR-3 agonists) and F protein of Respiratory Syncytial Virus (RSV).

Adjuvants in vaccines of the invention may typically include emollients, emulsifiers, thickening agents, preservatives, bactericides and buffering agents. Another type of "self adjuvant" is provided by the conjugation of immunogenic peptides to lipids such as the water soluble lipopeptides Pam3Cys or its dipalmitoyl derivative Pam2Cys. Such adjuvants have the advantage of accompanying and immunogenic component into the antigen presenting cell (such as dendritic cells) and thus producing enhanced antigen presentation and activation of the cell at the same time (see, for example, Brown and Jackson, (2005), "*Lipid based self adjuvanting vaccines*", Current Drug Delivery, 23:83).

Suitable adjuvants are commercially available such as, for example, Freund's Incomplete Adjuvant and Complete Adjuvant (Difco Laboratories, Detroit, Mich.): Merck Adjuvant 65 (Merck and Company, Inc., Rahway, N.J.): AS-2 (SmithKline Beecham. Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and Quil A. Cytokines, such as GM-CSF or interleukin-2, -7, or -12, may also be used as adjuvants.

In certain embodiments, an adjuvant included in a vaccine of the invention may induce an immune response predominantly of the Th1 type. Suitable adjuvants for use in eliciting a predominantly Th1-type response include, for example, a combination of monophosphoryl lipid A, preferably 3-de-O-acylated monophosphoryl lipid A (3D-MPL) together with an aluminum salt. For example, the composition or vaccine may be formulated with adjuvant AS04 containing aluminum hydroxide (alum) and 3-O-deacylated monophosphorylated lipid A (MPL) such as described in Thoelen et al. (2001), "*A prophylactic hepatitis B vaccine with a novel adjuvant system*", Vaccine, 19:2400-2403. Other known adjuvants, which preferentially induce a Th1 type immune response, include CpG containing oligonucleotides. The oligonucleotides are characterised in that the CpG dinucleotide is unmethylated. Such oligonucleotides are known to those of ordinary skill in the field and are described, for example, in PCT Publication No. WO 1996/02555. Immunostimulatory DNA sequences are also described, for example, in Sato et al., (1996), "*Immunostimulatory DNA sequences necessary for effective intradermal gene immunization*", Science, 273:352-354.

Another example of an adjuvant is a saponin, preferably QS21 (Aquila Biopharmaceuticals Inc., Framingham, Mass.), which may be used alone or in combination with other adjuvants. For example, an enhanced adjuvant system may be utilized involving the combination of a monophosphoryl lipid A and saponin derivative, such as the combination of QS21 and 3D-MPL as described in PCT Publication No. WO 1994/00153, or a less reactogenic composition where the QS21 is quenched with cholesterol, as described in PCT publication No. WO 1996/33739. Other alternative formulations comprise an oil-in-water emulsion and tocopherol. An adjuvant formulation involving QS21, 3D-MPL and tocopherol in an oil-in-water emulsion is described in PCT Publication No. WO 1995/17210. An adjuvant included in a composition of the invention may include a formulation involving QS21, 3D-MPL and tocopherol in an oil in water emulsion such as described in PCT publication No. WO 1995/17210. In one embodiment a composition of the invention comprises the adjuvant Montanide ISA720 (M-ISA-720; Seppic. Fairfield, N.J.), an adjuvant based on a natural metabolizable oil.

The adjuvant may be a mucosal adjuvant effective in enhancing mucosal immunity and/or systemic immunity to immunogenic components administered via the mucosal route. Mucosal adjuvants may be broadly classified as those that facilitate vaccine delivery (e.g. liposomes, cochleates, live-attenuated vectors, poly D,L-lactide-co-glycolide or PLGA, chitans, DNA vaccines, mucoadhesives) to enhance the induction of protective immunity induced by other immunogenic components of the vaccine, and those having an immunostimulatory role (e.g. innate immunity associated toxin-based, cytokine-based etc.). Without limitation to a particular mechanism, it is postulated that the advantageous effects of mucosal adjuvants partially derive from an ability to assist the passage of immunogenic components in the vaccine across the mucosal barrier. Upon traversing the mucosal barrier, the mucosal adjuvant may enhance immunity, for example, by complement activation, the induction of cytokines, stimulation of antibody production or antibody type switching, stimulating antigen presenting cells, and/or influencing MHC class I and/or class II expression.

Prophylactic and Therapeutic Methods

The present invention provides prophylactic methods for the inhibition or prevention of streptococcal infection in a subject. Also provided are therapeutic methods for treating streptococcal infection in a subject. The methods comprise administering the streptococcal bacteria and/or component/s thereof described herein (e.g. in the form of a pharmaceutical composition such as a vaccine).

The methods induce or enhance the immune response against streptococcal bacteria in the subject. The immune response may be cross-protective/heterologous insofar as it may induce or enhance the immune response against a plurality of serotypes of streptococcal bacteria. The methods may also comprise administering multiple different serotypes and/or species of the streptococcal bacteria described herein, to thereby generate immunity against multiple species of streptococcal bacteria and various serotypes thereof.

The methods may induce or enhance an immune response against pathogenic and/or non-pathogenic streptococcal bacteria. For example, the methods may induce or enhance an immune response against any one or more of the following streptococcal bacterial species and/or serotypes thereof. *Streptococcus acidominimus, Streptococcus agalactiae, Streptococcus alactolyticus, Streptococcus anginosus. Streptococcus australis, Streptococcus bovis, Streptococcus caballi, Streptococcus cameli, Streptococcus canis, Streptococcus caprae, Streptococcus castoreus, Streptococcus criceti, Streptococcus constellatus, Streptococcus cristatus, Streptococcus cuniculi, Streptococcus danieliae, Streptococcus dentasini, Streptococcus dentiloxodontae, Streptococcus dentirousetti, Streptococcus devriesei, Streptococcus didelphis, Streptococcus downei, Streptococcus dysgalactiae, Streptococcus entericus, Streptococcus equi, Streptococcus equinus, Streptococcus ferus, Streptococcus gallinaceus, Streptococcus gallolyticus, Streptococcus gordonii, Streptococcus halichoeri, Streptococcus halotolerans, Streptococcus henryi, Streptococcus himalayensis, Streptococcus hongkongensis, Streptococcus hyointestinats, Streptococcus hyovaginaas, Streptococcus ictaluri, Streptococcus infantarius, Streptococcus injintis, Streptococcus iniae. Streptococcus intermedius, Streptococcus lactarius, Streptococcus loxodontisahvarius, Streptococcus lutetiensis, Streptococcus macacae, Streptococcus marimammalium, Streptococcus*

*marmotae, Streptococcus massiliensis, Streptococcus merionis, Streptococcus minor, Streptococcus mitis, Streptococcus moroccensis, Streptococcus mutans, Streptococcus oralis, Streptococcus oricebi, Streptococcus oriloxodontae, Streptococcus orisasini, Streptococcus orisratti, Streptococcus orisuis, Streptococcus ovis, Streptococcus panodentis, Streptococcus pantholopis, Streptococcus parasanguinis, Streptococcus parasuis, Streptococcus parauberis, Streptococcus peroris, Streptococcus pharyngis, Streptococcus phocae, Streptococcus pluranimalium, Streptococcus plurextorum, Streptococcus pneumoniae, Streptococcus porci, Streptococcus porcinus, Streptococcus porcorum, Streptococcus pseudopneumoniae, Streptococcus pseudoporcinus, Streptococcus pyogenes, Streptococcus ratti, Streptococcus rifensis, Streptococcus rubneri, Streptococcus rupicaprae, Streptococcus salivarius, Streptococcus saliviloxodontae, Streptococcus sanguinis, Streptococcus sinensis, Streptococcus sobrinus, Streptococcus suis, Streptococcus tangierensis, Streptococcus thoraltensis, Streptococcus troglodyvtae, Streptococcus troglodytidis, Streptococcus tigurinus, Streptococcus thermophilus, Streptococcus uberis, Streptococcus urinalis, Streptococcus ursoris, Streptococcus vestibularis,* and *Streptococcus zooepidemicus.*

In some embodiments, the methods may induce or enhance an immune response against any one or more of the following pathogenic streptococcal bacterial species and/or serotypes thereof: *Streptococcus agalactiae, Streptococcus bovis, Streptococcus canis, Streptococcus dysgalactiae, Streptococcus equi, Streptococcus equinus, Streptococcus equisimilis, Enterococcus faecalis, Enterococcus faecium, Streptococcus iniae, S. milleri, Streptococcus mutans, Streptococcus pneumoniae, Streptococcus pyogenes, Streptococcus salivarius, Streptococcus sanguinis, Streptococcus suis* and *Streptococcus uberis.*

In some embodiments, the methods are utilized to inhibit, prevent or treat an infection, disease or condition caused by one or more serotypes of *Streptococcus pneumoniae.* The methods may comprise inducing an immune response in a subject against a plurality of different *Streptococcus pneumoniae* serotypes, by administering streptococcal bacteria or the present invention to the subject in the form of one or more serotypes of *Streptococcus pneumoniae*, which may induce immunity against any one of more of *Streptococcus pneumoniae* serotypes 1, 2, 3, 4, 5, 6A, 6B, 6C, 6D, 7A, 7B, 7C, 7F, 8, 9A, 9L, 9N, 9V, 10A, 10B, 10C, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22A, 22F, 23A, 23B, 23F, 24A, 24B, 24F, 25A, 25F, 27, 28A, 28F, 29, 31, 32A, 32F, 33A, 33B, 33C, 33D, 33F, 34, 35A, 35B, 35C, 35F, 36, 37, 38, 39, 40, 41A, 41F, 42, 43, 44, 45, 46, 47A, 47F, and/or 48. For example, immunity may be induced against any one or more of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F. The *Streptococcus pneumoniae* serotype(s) administered may differ from the serotype(s) causative of the infection, disease or condition.

The disease or condition may be any that is caused by infection of the particular species or serotype of streptococcal bacteria. By way of non-limiting example only, the disease or condition may be any one or more of: pneumonia, ear infection, earache, middle ear infection, otitis media, sinusitis, meningitis, conjunctivitis, bacteraemia, septicaemia, a joint infection, a bone infection, septic arthritis, osteomyelitis, a soft tissue infection, cellulitis, periorbital cellulitis, an abscess, peritonitis, a cardiac infection, endocarditis, and pericarditis.

The subject may be any animal of economic, social or research importance including bovine, equine, ovine, primate, avian and rodent species. Accordingly, the subject may be a mammal such as, for example, a human or a non-human mammal (e.g. a pig, cat, dog, cow, horse, or sheep). The subject may be a laboratory animal (e.g. a rodent such as a mouse, rat, or guinea pig; a rabbit, and the like), a bird (e.g. poultry), a fish or a crustacean.

The streptococcal bacteria and/or component/s thereof described herein (e.g. in the form of a pharmaceutical composition such as a vaccine) may be administered to the subject by any suitable route including, for example, parenteral (e.g. intradermal, intravenous, intraspinal, intraperitoneal, subcutaneous or intramuscular), oral, topical, or mucosal routes (e.g. intranasal). In some embodiments, administration is by the mucosal route. For example, the administration may be intranasal.

Without being limited to specific mechanism(s) of action, the vaccines and methods of the present invention may induce an immune response in the subject comprising one or more of the following:

(i) activation of the innate immune system including the production of cytokines (e.g. IFN-γ) and/or activation of Toll-like receptors (e.g. Toll-like receptor 2—TLR2);

(ii) production of antibodies that bind specifically to antigen(s) of the streptococcal bacteria causative of the infection, disease or condition;

(iii) opsonin-dependent phagocytosis (e.g. via opsonophagocytic activity (OPA) of streptococcal-specific antibodies)

(iv) $CD4^+$ T lymphocyte responses specific for antigen(s) of the streptococcal bacteria causative of the infection, disease or condition;

(v) $CD8^+$ T lymphocyte responses specific for antigen(s) of the streptococcal bacteria causative of the infection, disease or condition.

In some embodiments, the immune response induced by the vaccines and methods of the present invention may comprise activation of Toll-like receptor 2 (also known and referred to herein as TLR2). As known to persons skilled in the art, TLR2 recognises bacterial pathogens through bacterial cell wall components such as lipoteichoic acid or peptidoglycan. Without limitation, activation of TLR2 in a subject to which the vaccines of the present invention are administered may induce any one or more of: influx of neutrophils into the lungs, production of pro-inflammatory cytokines, activation of alveolar macrophages, and/or protection against meningitis and otitis media caused by streptococcal bacteria. Additionally or alternatively, activation of TLR2 in a subject to which the vaccines of the present invention are administered may shape adaptive immunity against streptococcal infection. For example, it may promote the prevalence of IgG antibody responses and in particular promote subclasses of IgG associated with TH1-type immune responses such as IgG3, IgG2a. IgG2b. Again without limitation, the prevalence of IgG subclasses such as, for example, IgG3, may promote opsonophagocytic activity and/or provide enhanced immunogenicity against streptococcal infection. The stimulation of TLR2 in CD4+ T helper cells is known to aid differentiation to $T_H17$ and promote the development of IL-17-producing CD4+ T cells to control streptococcal colonization and/or infection.

These and other immune responses induced by the streptococcal bacteria and/or component/s thereof described herein can be characterised and/or quantified using standard assays known in the art, and include, for example, solid-phase heterogeneous assays (e.g. enzyme-linked immunosorbent assay), solution phase assays (e.g. electrochemiluminescence assay), amplified luminescent proximity homogeneous assays, flow cytometry, intracellular cytokine staining, functional T-cell assays, functional B-cell assays, functional monocyte-macrophage assays, dendritic and reticular endothelial cell assays, measurement of NK cell responses, opsonophagocytic assays (OPAs), oxidative burst assays, cytotoxic specific cell lysis assays, pentamer binding assays, and phagocytosis and apoptosis evaluation. Suitable techniques are also described in the Examples of the present application.

By way of non-limiting example only, an immune response induced or enhanced in a subject by the method may be increased by at least about 10%, at least about 20%, at least about 25%, at least about 50%, at least about 75%, at least about 90%, at least about two-fold, at least about five-fold, at least about ten-fold, at least about twenty-fold, at least about fifty-fold, or at least about 100-fold, when compared to a suitable control. The suitable control may, for example, be a measurement of the same immune response prior to performing the method under otherwise similar, substantially identical, or identical conditions.

Routes of Administration

The streptococcal bacteria and/or component/s thereof described herein (e.g. in the form of pharmaceutical compositions such as vaccines) may be administered to a subject by standard routes, including, but not limited to, parenteral (e.g. intradermal, intravenous, intraspinal, intraperitoneal, subcutaneous or intramuscular), oral, topical, or mucosal routes (e.g. intranasal).

For example, they may be administered by a mucosal route. Non-limiting examples of acceptable routes of mucosal vaccine administration including intranasal, ocular, buccal, genital tract (vaginal), rectal, intratracheal, skin, and the gastrointestinal tract.

In some embodiments, they are administered by the intranasal route. Without limitation to theory or particular mode(s) of action, intranasal administration may be advantageous for enhancing immunity against certain streptococcal infections in which bacteria infect the host via mucosal surfaces of the upper and/or lower respiratory tracts. In addition, mucosal vaccination (e.g. intranasal vaccination) may induce mucosal immunity not only in the respiratory tracts but also in distant mucosal sites including the genital mucosa.

Intranasal vaccines of the invention can be formulated, for example, in liquid form as nose drops, spray, or suitable for inhalation, as powder, as cream, or as emulsion. Nebulised or aerosolised intranasal vaccines may also be utilized. Administration of vaccines to mucosa of the upper and/or lower respiratory tract via inhalation of mists, powders, or sprays, or by intranasal administration of nose drops, swabs, powders, sprays, mists, aerosols, and the like is also contemplated.

In one embodiment, the vaccines for intranasal administration are provided in a freeze-dried powder form capable of re-constitution immediately prior to use. Powder vaccine formulations of vaccines of the present invention provide a means of overcoming refrigerated storage and distribution requirements associated with liquid-based vaccine stability and delivery. Dry powder formulations offer the advantage of being more stable and also do not support microbial growth.

The freeze-dried vaccines may induce levels of hetero-subtypic immunity similar to that of non freeze-dried vaccines. The vaccines may be freeze-dried using any suitable technique known in the art. For example, liquid preparations of photon-irradiated streptococcal bacteria and/or derivatives thereof may be frozen in a dry ice—isopropanol slurry and lyophilized in a freeze Dryer (e.g. Virtis Model 10-324 Bench, Gardiner, NY) for a suitable time period (e.g. 24 hours).

In one embodiment, a dry powder nasal vaccine of the invention is produced by generating spray-freeze-drying (SFD) particles (see, for example, Costantino et al., (2002), "*Protein spray freeze drying. 2. Effect of formulation variables on particle size and stability*", J Pharm Sci., 91:388-395; Costantino, et al., (2000), "*Protein spray-freeze drying. Effect of atomization conditions on particle size and stability*", Pharm Res., 17:1374-1383: Maa et al., (1999), "*Protein inhalation powders: spray drying vs spray freeze drying*", Pharm Res, 16:249-254; Carrasquillo et al., (2001); "*Non-aqueous encapsulation of excipient-stabilized spray-freeze dried BSA into poly(lactide-co-glycolide) microspheres results in release of native protein*", J Control Release, 76.199-208; Carrasquillo et al., (2001), "*Reduction of structural perturbations in bovine serum albumin by non-aqueous microencapsulation*", J Pharm Pharmacol., 53:115-120; and U.S. Pat. No. 6,569,458).

Preferred devices for intranasal administration of the vaccines are nasal spray devices (e.g. devices available commercially from Pfeiffer GmBH, Valois and Becton Dickinson). Non-limiting examples of suitable devices are described, for example, in Bommer, (1999), "*Advances in Nasal drug delivery Technology*", Pharmaceutical Technology Europe, p 26-33. Intranasal devices may produce droplets in the range 1 to 500 $\mu m^3$. Preferably, only a small percentage of droplets (e.g. <5%) are below 10 $\mu m$ to minimise the chance of inhalation. Intranasal devices may be capable of bi-dose delivery, that is, the delivery of two subdoses of a single vaccination dose, one sub-dose to each nostril.

A vaccine of the present invention may be administered to a recipient in isolation or in combination with other additional therapeutic agent(s). In embodiments where the vaccine is administered with therapeutic agent(s), the administration may be simultaneous or sequential (i.e. vaccine administration followed by administration of the agent(s) or vice versa). Thus, where a vaccine of the present invention is administered to a subject in conjunction with another agent, both may be administered in a single composition at the same time, in separate compositions at the same time, or separately at different times.

Dosages

In general, vaccines of the present invention are administered in a manner compatible with the route of administration and physical characteristics of the recipient (including health status) and in such a way that it elicits the desired effect(s) (i.e, therapeutically effective, immunogenic and/or protective).

For example, the appropriate dosage of a given vaccine may depend on a variety of factors including, but not limited to, a subject's physical characteristics (e.g. age, weight, sex), whether the compound is being used as single agent or adjuvant therapy, the progression (i.e. pathological state) of a given streptococcal infection, and other factors that may be recognized by one skilled in the art. Various general considerations that may be considered when determining an appropriate dosage of a given vaccine of the invention are described, for example, in Gennaro et al. (Eds), (1990), "*Remington's Pharmaceutical Sciences*", Mack Publishing Co., Easton, Pennsylvania, USA: and Gilman et al., (Eds), (1990), "*Goodman And Gilman's: The Pharmacological Bases of Therapeutics*", Pergamon Press.

In general, vaccines of the present invention may be administered to a patient in an amount of from about 5 micrograms to about 5 mg of active component(s) (i.e, the streptococcal bacteria and/or component/s thereof as described herein). Dosage in an amount of from about 50 micrograms to about 1000 micrograms is especially preferred.

One skilled in the art would be able, by routine experimentation, to determine an effective, non-toxic amount of the streptococcal bacteria and/or component/s thereof to include in a vaccine of the present invention for the desired therapeutic outcome.

Typically, in therapeutic applications, the treatment would be for the duration of the infection, disease state or condition. Further, it will be apparent to one of ordinary skill in the art that the optimal quantity and spacing of individual dosages will be determined by the nature and extent of the infection, disease state or condition being treated, the form, route and site of administration, and the nature of the particular individual being treated. Also, such optimum conditions can be determined by conventional techniques.

In many instances, it will be desirable to have several or multiple administrations of a vaccine of present invention. For example, vaccines of the invention may be administered 1, 2, 3, 4, 5, 6, 7, 8, 9, 10, or more times. The administrations may be from about one to about twelve week intervals, and in certain embodiments from about one to about four week intervals. Periodic re-administration may be desirable in the case of recurrent exposure to a particular pathogen targeted by a vaccine of the invention.

It will also be apparent to one of ordinary skill in the art that the optimal course of treatment can be ascertained using conventional course of treatment determination tests.

The methods described herein may comprise administering a priming dose of a vaccine of the present invention. The priming dose may be followed by a booster dose. The booster may be for the purpose of revaccination. In various embodiments, the vaccine is administered at least once, twice, three times or more. Vaccines of the present invention may be administered to naïve recipients, being individuals seronegative for particular target strain(s) of streptococcal bacteria. Alternatively, the vaccines may be administered to primed recipients, being individuals seropositive for particular target strain(s) of streptococcal bacteria.

EXAMPLES

The present invention will be described with reference to specific Example(s) which should not be construed as in any way limiting.

Example One: Generation of a *Streptococcus pneumoniae* GPN-001 Strain Harbouring a Deletion of the psaC Gene The *Streptococcus pneumoniae* strain GPN-001 is a derivative of the Rx1 strain, which lacks the outer capsule of the bacterium and harbours a deletion of the autolysin A gene lyA, and replacement of the native pneumolysin gene ply with a gene encoding a toxoid version (PdT), designated GPN-001. A derivative of GPN-001, which harbours a deletion of the gene encoding the solute binding component of the manganese uptake ATP-binding cassette transporter, psaA was designated GPN-002.

A strain harbouring a deletion of the gene encoding permease protein of the manganese uptake ATP-binding cassette transporter, psaC was generated. The DNA sequence of the psaC gene, prior to deletion (including flanking regions), is shown in SEQ ID NO: 1.

An erythromycin resistance cassette was incorporated into this region by conventional methods of overlap extension PCR and transformation, shown in the flow chart of FIG. 1. Strain selection was based on the gain of an erythromycin resistance phenotype. This strain was designated *S. pneumoniae* GPN-001 Δpsa::ery$^R$). A deletion of the psaC gene was generated by transformation this strain with a DNA fusion construct (SEQ ID NO: 2) generated by overlap extension PCR of the upstream and downstream flanking regions. Enrichment of the deletion strain was achieved by culturing in the presence of erythromycin, followed by ampicillin treatment. Successful incorporation was determined by assessment of antibiotic resistance profile by patch testing on antibiotic- and un-supplemented blood agar plates, PCR and size analysis by agarose gel electrophoresis. The resulting strain, *S. pneumoniae* GPN-001 ΔpsaC, in which manganese acquisition is impaired by mutation of the transporter permease protein component of the uptake system, was designated GPN-001 ΔpsaC.

Example Two: Assessment of the Impact of Various Manganese-Modulating Mutations and Treatments During Growth on Cellular Manganese Abundance Experiments were performed to assess whether mutation of components of the manganese uptake system, treatment with zinc or EDTA, or omission of the manganese from the growth medium impacted cellular manganese abundance. The GPN-001, GPN-002 and GPN-001 ΔpsaC strains were grown to equivalent optical densities (OD$_{600}$~1.7) in standard medium (comprised of soytone medium with 2.14 μM manganese sulphate). The GPN-001 strain was grown to equivalent optical densities (OD$_{600}$~1.7) in standard medium supplemented with either 600 μM zinc sulphate (+Zn) or 500 μM EDTA (+EDTA), or in standard medium with the 2.14 μM manganese sulphate omitted (No Mn). The cells were washed twice with 20 ml ice-cold phosphate buffered saline (PBS) supplemented with 5 mM Ethylenediaminetetraacetic acid (EDTA) and washed twice with 20 ml ice-cold PBS. Cellular material was desiccated at 96° C. and the dry weight of the material was measured. Dried cellular material was treated with 1 ml 35% HNO$_3$, heated at 96° C. for 1 hr. diluted 1:10 in milliQ water, and analysed for manganese abundance by inductively coupled plasma-mass spectrometry (ICP-MS) on an Agilent 8900 ICP-QQQ (Adelaide Microscopy).

The concentration of manganese was determined by ICP-MS based on counts per second (CPS) measurements with a calibration curve of known concentrations (High-Purity Standards, US) and internal indium control. The concentration in parts per billion (ppb) was derived from the CPS data and the concentration of manganese relative to cellular material was calculated (FIG. 2). Data are the mean (i SEM) manganese concentration represented in microgram (μg) per gram (g) of cell material from three independent growth experiments.

Comparisons of the manganese abundance showed that GPN-002, GPN-001 ΔpsaC, GPN-001+Zn and GPN-001+EDTA accumulated ~75% less cellular manganese relative to GPN-001. Growth of GPN-001 with the manganese omitted from the growth medium showed ~25% reduction in total cellular manganese relative to GPN-001 grown in standard medium.

Example Three: Assessment of the Impact of Various Manganese-Modulating Mutations and Treatments During Growth on the Transcription of the Manganese Responsive Gene prtA Quantitative reverse transcription-PCR (qRT-PCR) was performed to assess whether mutation of psaA or psaC, or growth in soytone medium with zinc, EDTA or with manganese omitted induced changes in the expression of the manganese-responsive gene prtA.

Figure 3:
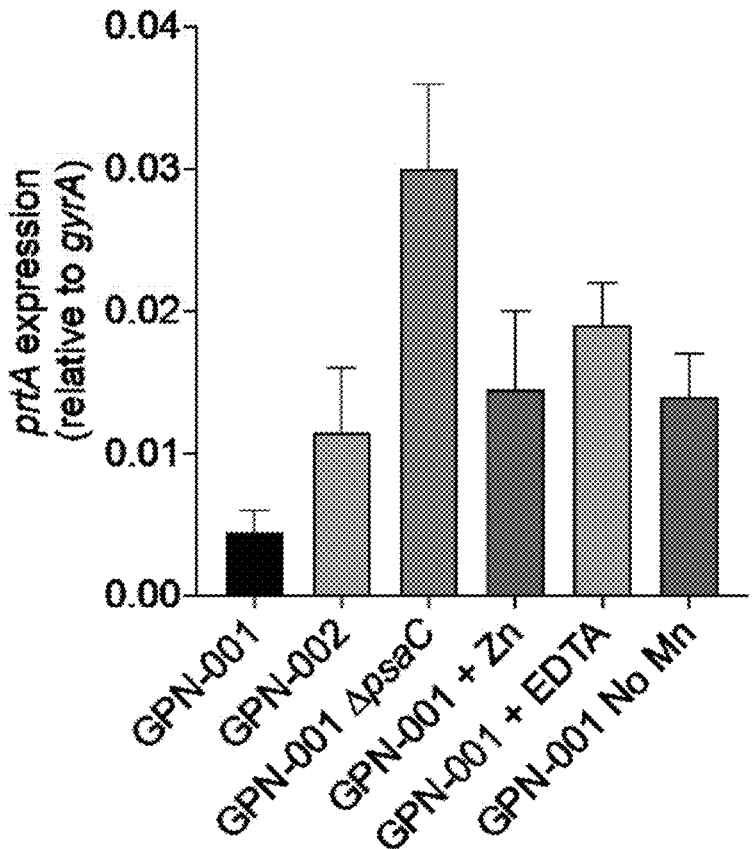
FIG. 3 shows the expression of the prtA gene relative to the internal control gyrA gene by quantitative reverse transcription-polymerase chain reaction. The data demonstrates that deletion mutation of the solute binding protein (psaA; strain GPN-002), or the permease protein (psaC; strain GPN-001 ΔpsaC), or growth of strain GPN-001 in the presence of zinc, EDTA or with manganese omitted from the growth medium results in an increase in prtA transcription relative to the GPN-001 strain grown under the standard conditions. Data are the mean expression relative gyrA.

The GPN-001, GPN-002 and GPN-001 ΔpsaC strains were grown to equivalent optical densities (OD$_{600}$~0.6) in standard medium (comprised of soytone medium with 2.14 μM manganese sulphate). The GPN-001 strain was grown to equivalent optical densities (OD$_{600}$~0.6) in standard medium supplemented with either 600 μM zinc sulphate (+Zn) or 500 μM EDTA (+EDTA), or in standard medium with the 2.14 μM manganese sulphate omitted (No Mn). Culture samples were immediately transferred to RNAProtect Bacteria Reagent (Qiagen) and incubated for 5 mins at room temperature. The cellular material was centrifuged, the supernatant removed, and the pellets were stored at −80° C. The cells were enzymatically lysed with lysozyme and mutanolysin and the RNA was extracted using the RNeasy Mini Kit (Qiagen) with an on-column DNase I treatment (Qiagen) according to the manufacturer's instructions. Total RNA was quantified using the LVis plate on a PHERAStar Omega (BMG Labtech) and diluted to 20 ng/μl. The qRT-PCR was performed using the SuperScript III One-Step RT-PCR kit (Invitrogen) kit and the QuantStudio 6 Flex Real-Time PCR System (Thermofisher Scientific). Primers for the amplification of a ~150 bp sequence of prtA were designed using the UGENE extension Primer3 (prtA_F 5-AAGAAAAGCAGGCATTCCAA-3'—SEQ ID NO: 3; and prtA_R 5'-GCAGAAGCGACCGCTATCGC-3'—SEQ ID NO: 4). The levels of gene transcription were normalised to the gyrase A gene (gyrA) using primers gyrA_F 5'-ACTGGTATCGCGGTTGGGAT-3'—SEQ ID NO: 5) and gyrA_R 5'-ACCTGATTTCCCCATGACAA-3'—SEQ ID NO: 6). Data are presented as the mean transcription relative to gyrA (FIG. 3).

Comparisons of the expression of the manganese-responsive gene prtA showed higher expression in GPN-002, GPN-001 ΔpsaC, GPN-001+Zn, GPN-001+EDTA and GPN-001 no Mn relative to GPN-001 grown in the standard medium.

Example Four: Assessment of the Impact of Various Manganese-Modulating Mutations and Treatments During Growth on Toll-Like Receptor 2 (TLR2) Activation The impact of intracellular manganese limitation on the ability of streptococcal bacteria to activate innate receptor TLR2 was tested using an in vitro stimulation assay.

The GPN-001, GPN-002 and GPN-001 ΔpsaC strains were grown to equivalent optical densities (OD$_{600}$~1.7) in standard medium (comprised of soytone medium with 2.14 μM manganese sulphate). The GPN-001 strain was grown to equivalent optical densities (OD$_{600}$~1.7) in standard medium supplemented with either 600 μM zinc sulphate (+Zn) or 500 μM EDTA (+EDTA), or in standard medium with the 2.14 μM manganese sulphate omitted (No Mn). The cells were washed and re-suspended in ice-cold PBS-13% glycerol and immediately frozen at −80° C.

Figure 4:
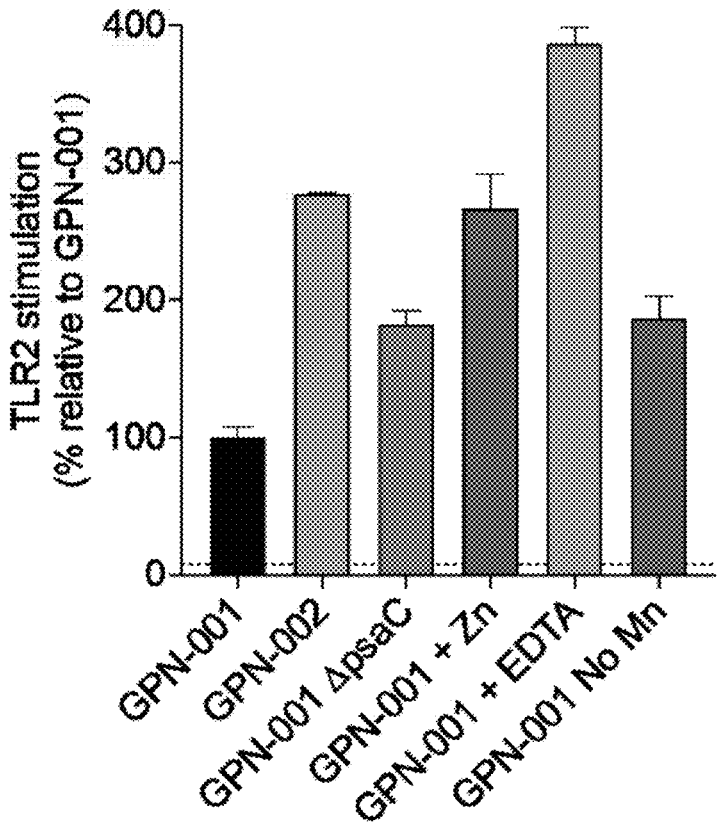
FIG. 4 depicts the stimulation of Toll-like receptor 2 (TLR2) by streptococcal bacteria grown with the indicated treatments or in strains possessing mutations in genes encoding components of the manganese uptake pathway. These data reveal that deletion mutation of the solute binding protein (psaA; strain GPN-002), or the permease protein (psaC: strain GPN-001 ΔpsaC), or growth of strain GPN-001 in the presence of zinc. EDTA or with the manganese omitted from the medium confers higher TLR2 stimulation compared with GPN-001 grown under the standard conditions. Data are the mean percent difference in TLR2 stimulation compared with GPN-001 from technical duplicates.

The total protein concentration was determined by Bio-Rad DC Protein Assay and 10 μg/ml was used to stimulate the HEK-blue reporter HEK-293 cells stably expressing human TLR2 (FIG. 4). A concentration of 0.0625 μg/ml of the bacterial lipoprotein Pam3CSK4 was used as a positive control for TLR2 stimulation (data not shown). The blank-corrected absorbance at 655 nm ($OD_{655}$) was determined at 16 hrs from n=2 technical replicates. Data are presented as the mean percentage TLR2 stimulation (±SEM) relative to the GPN-001 strain. The dotted line indicates the mean response observed for the negative control (PBS+13% glycerol).

HEK-blue TLR2 cells stimulated with GPN-002, GPN-001 ΔpsaC, GPN-001+Zn, GPN-001+EDTA and GPN-001 no Mn showed higher TLR2 stimulation relative to GPN-001 grown under the standard medium conditions. These data suggest that disruptions in manganese uptake resulted in enhanced TLR2 signalling in vitro.

Example Five: The Effect of Manganese Limitation on Toll-Like Receptor (TLR) Signalling The effect of live and irradiated GPN-001 and GPN-002 to activate the innate receptor TLR2 was tested using an in vitro stimulation assay. GPN-001 and GPN-002 were grown to equivalent optical density in THY broth, then washed and re-suspended in PBS+13% glycerol, immediately frozen at −80c and then subjected to inactivation with 16 kGy of gamma-irradiation. Samples remained frozen on dry ice during the inactivation process. Treated samples (denoted 'gamma'), and non-treated controls (denoted 'live') of GPN-001 and GPN-002 were then used to stimulate HEK-293 cells stably expressing human TLR2 or human TLR4. Heat-killed *Escherichia coli*, and heat-killed *S. pneumoniae* strains D39 (serotype 2), and Rx1 (non-encapsulated D39 derivative) were included as positive controls. All bacterial preparations were added to HEK-293 cells as whole cell pneumococci at 10 μg total protein/mL (as determined by BCA protein assay). Production of human IL-8 (μg/mL) in culture supernatants after 24 h of incubation with antigens was then determined by ELISA (FIGS. 5A-5B).

Data are presented as mean IL-8 pg/mL±S.D. (n=6 individual supernatant samples per antigen), and analyzed by two-way ANOV A (*P<0.05; **P<0.01). Dotted line indicates IL-8 production in the absence of any antigen, data compiled from two independent experiments.

Manganese limitation had no effect on TLR4 signalling (lower FIG. 5B), but was associated with clear enhancement for TLR2 signalling (upper FIG. 5A). Innate signalling was not reduced after irradiation treatment, as live and irradiated GPN-002 induced comparable TLR activation. GPN-002 was thus shown to induce enhanced TLR2 signalling in vitro.

Example Six: Analysis of Antibody Reactivity Against Lysates of Pneumococci Using Serum from Mice Vaccinated with GPN-001 and GPN-002

The antibody profile of serum raised in mice from GPN-001 (manganese replete) and GPN-002 (manganese deplete) was assessed. To assess the effect of manganese limitation on antibody reactivity profiles, mice were vaccinated and the resulting immune sera used to probe Western Blots of various streptococcal bacteria lysates. Samples of GPN-001 and GPN-002 vaccines and of encapsulated pneumococcal isolates (serotype 2 strain D39, and serotype 6A strain P9) were lysed by sonication, and 20 μg total protein of each lysate (determined by BCA protein assay) was loaded per well in duplicate for SDS-PAGE. Separated proteins were transferred to nitrocellulose membranes and probed with pooled immune sera from outbred Swiss mice vaccinated intranasally with GPN-001 or GPN-002 (n=10 individual mice per vaccine group). For immunizations, mice were vaccinated with two doses of GPN-001 or GPN-002 (21.25 μg total protein/dose), administered two weeks apart. Two weeks post-second immunization, sera were harvested from all animals.

Figure 6A:
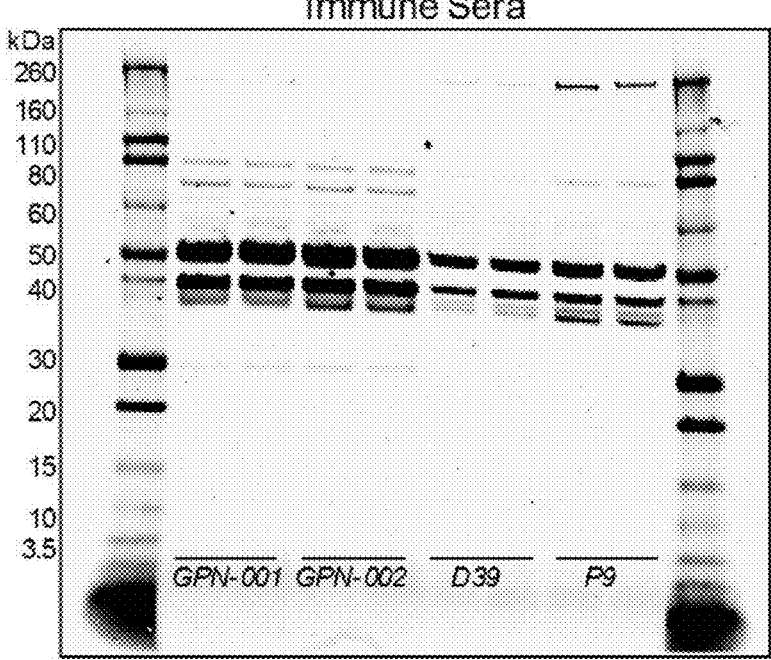
FIGS. 6A and 6B show Western blot indicative of antibody reactivity against lysates of different pneumococci using serum from mice vaccinated with streptococcal bacteria according to embodiments of the present invention.
Figure 6B:
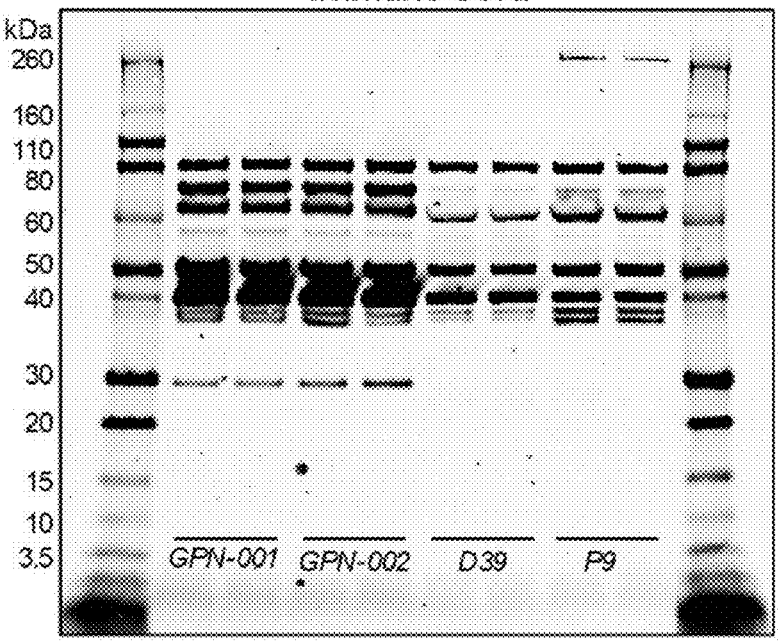

After probing membranes with pooled immune sera against GPN-001 or GPN-002, bound primary IgG was detected using IRDye 800CW goat anti-mouse IgG conjugate, and fluorescence was visualized using a LI-COR Odyssey imaging system (FIGS. 6A-6B). Novex Sharp Pre-Stained Protein Standard was run on all gels for size comparison. Data are representative of two independent experiments.

Direct comparison of antibody reactivity showed GPN-002-induced antibodies (lower image (B)) were able to bind to a larger number of pneumococcal proteins present in cell lysates than GPN-001-induced antibodies (upper image (A)).

Example Seven: Immunity in Mice Vaccinated with GPN-002 Following Homologous Challenge with *Streptococcus pneumoniae* Serotype 2 (Strain D39) and Heterologous Challenge with *Streptococcus pneumoniae* Serotype 6A (Strain P9)

To determine if the manganese-limited GPN-002 was able to confer protection against homotypic serotype 2 (strain D39) and heterologous serotype 6A (strain P9), mice were vaccinated intranasally with two doses of GPN-001 or GPN-002 (21.25 μg total protein/dose), administered two weeks apart. Control mice received intranasal PBS-mock vaccinations. Two weeks post-second vaccination, mice were challenged intranasally with 106 CFU/mouse of serotype 2 (homologous, strain D39) or $10^7$ CFU/mouse of serotype 6A (heterologous, strain P9). All mice were monitored for 3 weeks for development of clinical symptoms and overall survival. Data points in FIGS. 7A-7B indicate the survival time for each mouse (n=10-11 per group), and horizontal bars indicate the median survival time for each group. Differences in survival time were analyzed by Mann-Whitney U-test (*P<0.05).

GPN-002 was able to provide significant protection against lethal challenge with *Streptococcus pneumoniae* D39 (panel A) and *Streptococcus pneumoniae* 6A (panel B), shown by a significant difference in median survival compared to PBS-Mock control animals. Furthermore, GPN-002 afforded better protection against pneumococcal challenges than GPN-001.

Example Eight: Induction of *S. pneumoniae*-Specific Serum Antibody Responses in Rabbits Intramuscularly Vaccinated with GPN-002

To determine if GPN-002 could induce serum antibody responses in rabbits, immunization experiments were conducted.

Figure 8:
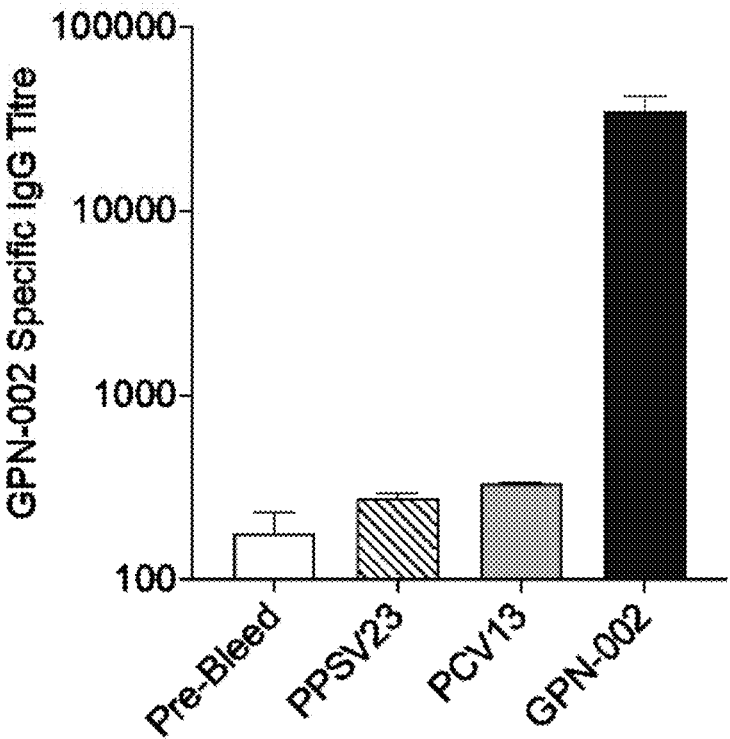
FIG. 8 provides graphs showing results of ELISA assays measuring IgG antibody titers in rabbits vaccinated with streptococcal bacteria according to embodiments of the present invention. Data presented as IgG titers pre-immunization and post-3' immunization for each individual rabbit, and as mean IgG titers (±SD) within each vaccine group. Data is compiled from two independent immunization experiments.

Outbred rabbits were intramuscularly (I.M.) vaccinated with GPN-002 (250 μg total protein in 0.5 mL PBS per rabbit), or with the commercially available Prevnar13 (PCV13) or Pneumovax23 (PPSV23) (0.5 mL per rabbit, equivalent to one human dose). Rabbits received three immunizations 3 weeks apart of either GPN-002 or PCV13, or received a single dose only of PPSV23 to mimic the human vaccination schedule. Serum was taken from all rabbits prior to immunizations (denoted as 'pre-bleed'), and 3 weeks after the final immunization. Individual serum samples were tested for total IgG by direct ELISA, using unirradiated GPN-002 as the capture antigen. FIG. 8 shows IgG titers pre-immunization and post-third immunization for each individual rabbit (upper panel (A)), and as mean IgG titers (±S.D.) (lower panel (B)) within each vaccine group. Data are compiled from two independent immunization experiments.

There were high-titer antibody responses detected to GPN-002 following I.M. immunization of rabbits. Comparatively, PCV13 and PPSV23 did not induce detectable antibody titers against pneumococcal proteins present on the surface of the un-encapsulated GPN-002 antigen.

Example Nine: Binding Affinity of GPN-002-Induced Antibodies for Encapsulated *S. pneumoniae* Isolates To assess whether GPN-002-specific antibodies (which target sub-capsular pneumococcal proteins) could also bind to fully encapsulated *S. pneumoniae* isolates, flow cytometry analysis was performed.

To generate antibodies for this analysis, rabbits were immunized I.M. with GPN-002 (250 μg total protein in 0.5 mL PBS per rabbit), or with the commercially available Prevnar13 (PCV13) or Pneumovax23 (PPSV23) (0.5 mL per rabbit, equivalent to one human dose). Rabbits received three immunizations 3 weeks apart of either GPN-002 or PCV13, or received a single dose only of PPSV23 to mimic the human vaccination schedule. Serum was taken from all rabbits prior to immunizations (pre-bleed), and also 3 weeks after the final immunization. Pre-bleed sera was pooled (n=8 rabbits total), as was post-immunization sera within each vaccine group (n=2-4 rabbits per group). Pooled sera were tested for IgG binding to multiple encapsulated pneumococcal strains using flow cytometry. A PCV13-included and PPSV23-included serotype was tested (serotype 14), as were PPSV23-specific serotypes (serotype 2 and serotype 22F), and a unique serotype included in neither PCV13 or PPSV23 (serotype 35B).

Figure 9:
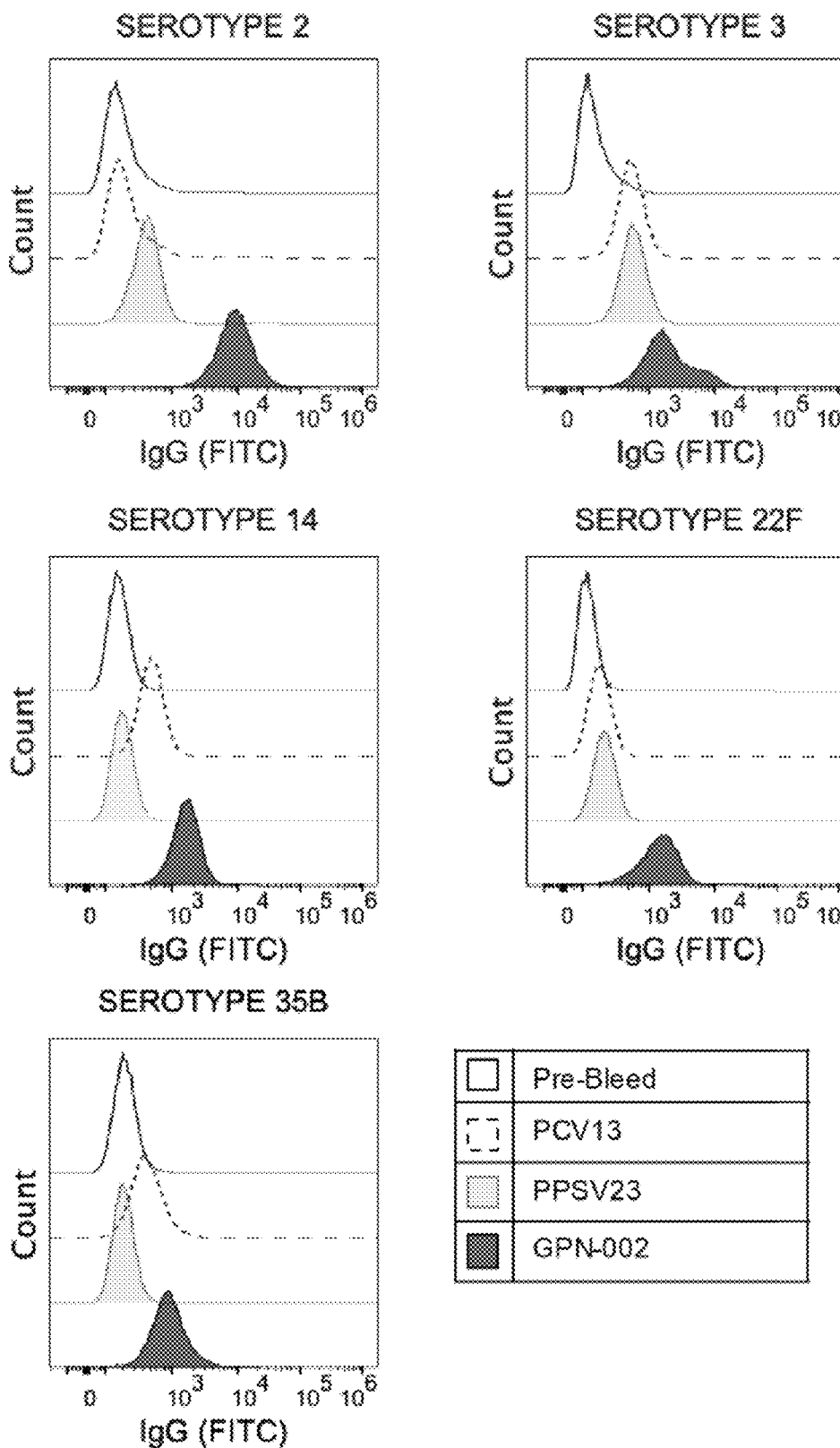
FIG. 9 provides flow cytometry histogram plots demonstrating that streptococcal bacteria according to embodiments of the present invention induce antibodies with high binding affinity for multiple encapsulated pneumococcal serotypes.

Briefly, $1 \times 10^7$ CFU of each pneumococcal serotype were incubated with pooled rabbit sera at a 1:200 dilution in PBS-BSA. Bacterial cells were pelleted and washed twice, and any primary IgG bound to the pneumococcal surface was then detected with an anti-rabbit IgG secondary antibody (FITC-conjugated). Histograms in FIG. 9 show the relative fluorescence detected by flow cytometry after incubation of each serotype with pooled rabbit sera for each vaccine group. Here, higher fluorescence is indicative of more IgG binding to the *S. pneumoniae* surface.

Results show that even in the presence of capsule, GPN-002-induced antibodies are able to bind to multiple pneumococcal serotypes with high affinity. Furthermore, the level of binding detected with GPN-002-specific antibodies was higher than that detected with PCV13- and PPSV23-induced antibodies for all tested serotypes.

Example Ten: Analysis of GPN-002-Induced Antibody Functionality in Mediating Opsonophagocytic Killing of Encapsulated *S. pneumoniae* Isolates Host protection against pneumococcal infections is mainly mediated by opsonin-dependent phagocytosis.

Therefore, opsonophagocytic killing activity (OPKA) of pneumococcal-specific antibodies is considered a crucial in vitro measure of functional antibody activity. OPKA titers were determined following vaccination of rabbits with GPN-002, and compared to titers achieved with the commercially available PCV13 and PPSV23.

Rabbits were immunized I.M. with GPN-002 (250 μg total protein in 0.5 mL per rabbit), or the commercially available Prevnar13 (PCV13) or Pneumovax23 (PPSV23) (0.5 mL per rabbit, equivalent to one human dose). Rabbits received three immunizations 3 weeks apart of either GPN-002 or PCV13, or received a single dose only of PPSV23 to mimic the human vaccination schedule. Serum was taken from all rabbits prior to immunizations (pre-bleed), and 3 weeks after the final immunization. Individual serum samples were tested for OPKA against a panel of pneumococcal serotypes, using the opsonophagocytic killing assay protocol established by Nahm et al (https://www.vaccine.uah.edu/UAB-MOPA.pdf).

Tables One and Two present mean OPKA titers for a panel of encapsulated *S. pneumoniae* serotypes. Titers were determined as the highest 3-fold serial dilution of rabbit serum giving 50% or more killing of the input CFU. Where no killing was detected with neat serum (1:4 dilution when mixed with other assay components), this is denoted as a titer of ≤4. Data are presented from two independent immunization and OPKA screening experiments.

Results show that GPN-002 induces comparable OPKA responses to PCV13 and PPSV23 against many vaccine-included pneumococcal serotypes, and superior responses to multiple non-included pneumococcal serotypes.

TABLE ONE

| Data Set 1 - Batch 1 Rabbit Sera | | | |
| --- | --- | --- | --- |
| Serotype | Pre-Bleed OPKA Titer | PCP13 OPKA Titer | GPN-002 OPKA Titer |
| PCV13 Serotypes | | | |
| 3 | ≤4 | 12 | 12 |
| 6A | ≤4 | 2,916 | 8,748 |
| 23F | 12 | 2,916 | 2,916 |
| PPSV23 Serotypes (non-PCV13) | | | |
| 2 | ≤4 | ≤4 | 12 |
| 9N | 36 | 108 | 2,916 |
| 11A | ≤4 | 12 | 8,748 |
| 22F | ≤4 | ≤4 | 2,916 |
| 33F | ≤4 | ≤4 | 324 |
| Non-PCV13, non-PPSV23 Serotypes | | | |
| 15A | ≤4 | 12 | 8,748 |
| 23A | ≤4 | 972* | 972 |
| 23B | ≤4 | 4 | 12 |
| 35B | ≤4 | ≤4 | 972 |

*cross-reactivity of PCV13 (which includes 23F) against the non-included 23A has been reported in the literature.

TABLE TWO

| Data Set 2 - Batch 2 Rabbit Sera | | | |
| --- | --- | --- | --- |
| Serotype | Pre-Bleed OPKA Titer | PPSV23 OPKA Titer | PCV13 OPKA Titer | GPN-002 OPKA Titer |
| PCV13 Serotypes | | | | |
| 6A | 12 | 12 | 108 | 2,916 |
| 23F | 12 | 36 | 972 | 972 |

TABLE TWO-continued

| | Data Set 2 - Batch 2 Rabbit Sera | | | |
|---|---|---|---|---|
| Serotype | Pre-Bleed OPKA Titer | PPSV23 OPKA Titer | PCV13 OPKA Titer | GPN-002 OPKA Titer |
| | PPSV23 Serotypes (non-PCV13) | | | |
| 2 | ≤4 | ≤4 | ≤4 | 12 |
| 9N | 972 | 972 | 2,916 | 78,732 |
| 11A | ≤4 | 12 | ≤4 | 324 |
| 22F | ≤4 | 2,916 | 324 | 26,244 |
| 33F | ≤4 | ≤4 | ≤4 | 36 |
| | Non-PCV13, non-PPSV23 Serotypes | | | |
| 6C | 12 | 36 | 324 | 972 |
| 15A | ≤4 | ≤4 | 12 | 2,916 |
| 23A | ≤4 | ≤4 | 36 | 108 |
| 23B | ≤4 | ≤4 | ≤4 | 12 |
| 35B | ≤4 | 12 | 12 | 108 |

Example Eleven: Analysis of Various Inactivation Methods on TLR2 Activation by GPN-002

The impact of various methods of bacterial inactivation on TLR2 stimulation was assessed. GPN-002 was grown to $OD_{600}$~1.7 in soytone medium supplemented with 2.14 µM manganese, washed and re-suspended in ice-cold PBS-13% glycerol and immediately frozen at −80° C. The material was inactivated by gamma irradiation (16 kGy, dry ice), formalin (2%, 5 minutes), or heat (70° C., 10 mins). All samples were washed and re-suspended in ice-cold PBS.

Figure 10:
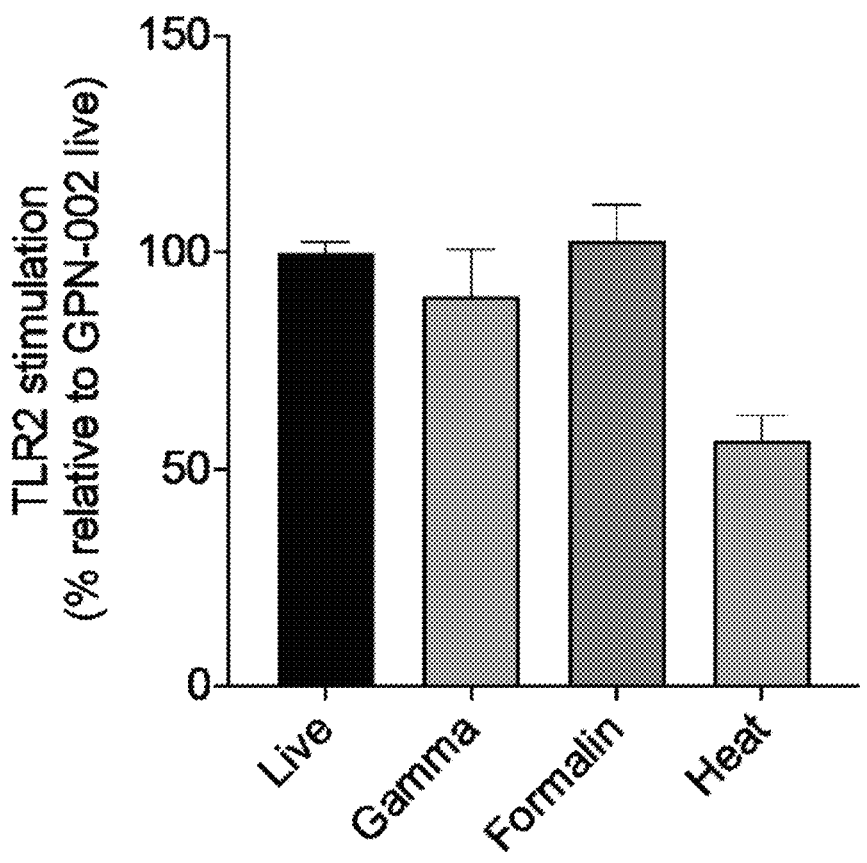
FIG. 10 shows the stimulation of Toll-like receptor 2 (TLR2) by live streptococcal bacteria (GPN-002), or bacteria (GPN-002) inactivated by gamma irradiation, formalin, or heat treatment.

The ability to activate the innate receptor TLR2 was then tested using an in vitro stimulation assay. The total protein concentration was determined by Bio-Rad DC Protein Assay and 10 µg/ml was used to stimulate the HEK-blue reporter HEK-293 cells stably expressing human TLR2 (FIG. 10). The blank-corrected absorbance at 655 nm ($OD_{655}$) was determined at 16 hrs from n=3 technical replicates. Data are presented as the mean percentage TLR2 stimulation (±SEM) relative to the live GPN-002 strain.

These data show that *Streptococci* killed by gamma-, formalin- or heat-inactivation each exhibited the ability to activate TLR2.

Example Twelve: Assessment of the Impact of Various Manganese-Modulating Mutations and Treatments During Growth on Immune Responses and Protective Efficacy Example twelve is prophetic.

To test additional manganese-modulating mutations and treatments during growth on immune responses and protective efficacy, GPN-001, GPN-002 and GPN-001 ΔpsaC strains can be grown to equivalent optical densities (e.g. $OD_{600}$~1.7) in standard medium (comprising, for example, soytone medium with 2.14 µM manganese sulphate). Additionally, the GPN-001 strain can be grown to equivalent optical densities (e.g. $OD_{600}$~1.7) in standard medium supplemented with, for example, either 600 µM zinc sulphate (+Zn) or 500 µM EDTA (+EDTA), or in standard medium with the manganese sulphate omitted (i.e. no Mn). The cells can be washed and re-suspended in ice-cold PBS-13% glycerol and immediately frozen (e.g. at −80° C.). Live attenuated or inactivated vaccines can be administered to subjects (e.g. mice or rabbits) and assessed for immune responses and protective efficacy.

For example:

Antibody responses can be assessed according to the methodology described in Example Six above. It is envisaged that vaccination with the GPN-002 and GPN-001 ΔpsaC strains will result in the production of antibodies against a wider range of pneumococcal proteins compared with GPN-001.

Protective immunity can be assessed using the methodology of Example Seven above. It is expected that vaccination with the GPN-002 and GPN-001 ΔpsaC strains will provide superior protection against challenge with live pneumococcal bacteria than GPN-001.

The induction of *S. pneumoniae*-specific serum antibody responses can be assessed using the methods described in Example Eight above. It is expected that antibodies induced by the GPN-002 and GPN-001 ΔpsaC strains would be capable of binding to multiple pneumococcal serotypes.

Antibody titers against pneumococcal proteins arising from immunization with the GPN-002 or GPN-001 ΔpsaC strain can be assessed according to the methodology described in Example Nine above. It is anticipated that vaccination with the GPN-002 or GPN-001 ΔpsaC strain will provide higher *S. pneumoniae*-specific IgG responses compared to those of currently used pneumococcal vaccines.

Antibody functionality in mediating opsonophagocytic killing of encapsulated *S. pneumoniae* isolates can be assessed using the methods set out in Example Ten above. It is expected that the GPN-002 or GPN-001 ΔpsaC strains w-ill provide comparable OPKA responses to PCV13 and PPSV23 against many vaccine-included pneumococcal serotypes, and superior responses to multiple non-included pneumococcal serotypes.

Example Thirteen: Assessment of the Impact of Vaccine Strains Overexpressing mntE, mgtA or psaR Genes, or Grown in the Presence of Metal Ionophores on Manganese Content, Gene Expression, TLR2 Stimulation, Immune Responses and Protective Efficacy Example thirteen is prophetic.

Strains overexpressing the mntE, mgtA or psaR genes can be constructed in the *S. pneumoniae* GPN-401 strain. Overexpression strains can be constructed by transformation with plasmids introducing tagged copies of the mntE, mgtA or psaR genes under the control of a constitutive promoter. The resulting strains, GPN-001 mntE⁺, GPN-001 mgtA⁺, and GPN-001 psaR⁺, may then be assessed for manganese content, gene expression, TLR2 stimulation, immune responses, and protective efficacy.

For example:

GPN-001 mntE⁺, GPN-001 mgtA⁺, and GPN-001 psaR⁺ can be assessed for the expression of the manganese-responsive gene prA using the methodology set out in Example Two above. It is expected that these strains will exhibit higher expression relative to GPN-001 grown in the standard medium.

GPN-001 mntE⁺, GPN-001 mgtA⁺, and GPN-001 psaR⁺ can be assessed for manganese content using the directions set out in Example Three above. It is envisaged that these strains will accumulate significantly less manganese relative to GPN-001.

The impact of GPN-001 mntE⁺, GPN-001 mgA⁺, or GPN-001 psaR⁺ on the ability of streptococcal bacteria to activate innate receptor TLR2 can be tested, for example, using the in vitro stimulation assay described in Example four above. TLR2 cells stimulated with these strains are expected to show higher TLR2 stimulation relative to GPN-001 grown under the standard medium conditions.

Immune responses arising from GPN-001 mntE⁺, GPN-001 mgA⁺, and GPN-001 psaR⁺ can be assessed by any suitable means, including for example the methodology set out in any one or more of Examples Six to Eleven above. It is envisaged that GPN-001 mntE⁺. GPN-001 mgtA⁺, and GPN-001 psaR⁺ will display any one or more of: antibody production against a wider range of pneumococcal proteins compared with GPN-001; superior protection against challenge with live pneumococcal bacteria than GPN-001; production of antibodies capable of binding to multiple pneumococcal serotypes; higher *S. pneumoniae*-specific IgG responses compared to those of currently used pneumococcal vaccines: comparable OPKA responses to PCV13 and PPSV23 against many vaccine-included pneumococcal serotypes, and superior responses to multiple non-included pneumococcal serotypes; and/or activation of TLR2.

---

The invention claimed is:

1. A vaccine composition comprising at least one of (i), or (ii):

(i) attenuated or killed streptococcal bacteria that were cultured in a manner that restricts levels of intracellular manganese ions ($Mn^{2+}$), wherein the attenuated or killed streptococcal bacteria are either (a) attenuated streptococcal bacteria that express a wild-type PsaA protein or a functional homolog of PsaA at equivalent or increased levels as compared to wild-type forms of the streptococcal bacteria, or (b) killed streptococcal bacteria that, prior to being killed, express a wild-type PsaA protein or a functional homolog of PsaA at equivalent or increased levels as compared to wild-type forms of the streptococcal bacteria;

and/or (ii) immunogenic components obtained from (i).

2. The composition of claim 1, wherein the attenuated or killed streptococcal bacteria were cultured:

(i) with an ionophore to thereby increase cellular uptake of cations selected from at least one of: $Zn^{2+}$, $Cu^{2+}$, $Co^{2+}$, $Ni^2$, $Fe^{2+}$, and $Cd^{2+}$; or (ii) with an ionophore to thereby increase cellular uptake of cations selected from at least one of: $Zn^{2+}$, $Cu^{2+}$, $Co^2$, $Ni^{2+}$, $Fe^{2+}$, and $Cd^{2+}$ and the ionophore is selected from at least one of: pyrithione, 8-hydroxyquinoline, and an analogue thereof; or (iii) in media comprising cations that compete with manganese ion binding sites on the bacteria.

3. The composition of claim 2, wherein:

(i) the cations comprise at least one of: $Zn^{2+}$, $Cu^{2+}$, $Co^{2+}$, $Ni^{2+}$, $Fe^{2+}$, and $Cd^{2+}$; or (ii) the cations interact with a streptococcal protein selected from: MgtA riboswitch and functional homologs thereof;

to thereby alter regulation of manganese transport genes in the bacteria; or (iii) the cations interact with a streptococcal protein selected from: MgtA riboswitch and functional homologs thereof;

to thereby increase cellular uptake of the cations in the bacteria; or (iv) the attenuated or killed streptococcal bacteria were cultured in media comprising a molar excess of the cations sufficient to inhibit PsaA protein function.

4. The composition of claim 1, wherein the attenuated or killed streptococcal bacteria were cultured with at least one of: a chelating agent, and an adsorption agent;

to thereby reduce the availability of manganese ions to the bacteria.

5. The composition of claim 4, wherein:

(i) the agent is selected from at least one of: Ethylenediaminetetraacetic acid (EDTA), trans-1,2-Diaminocyclohexane-N,N,N',N'-tetraacetic acid (CyDTA), N,N,N',N'-tetrakis(2-pyridinylmethyl)-1,2-ethanediamine (TPEN), and Calprotectin; or (ii) the attenuated or killed streptococcal bacteria were cultured in media pretreated with a cation chelating resin comprising styrene divinylbenzene copolymer containing paired iminodiacetate ions.

6. The composition of claim 1, wherein the attenuated or killed streptococcal bacteria were cultured in:

(i) any of:

media without manganese ions, media depleted of manganese ions, media with minimal manganese ions sufficient to support growth of the bacteria; or (ii) media comprising an antagonist of at least one streptococcal protein selected from: PsaA, PsaB, PsaC, PsaR, MntE, and functional homologs thereof; or (iii) media comprising an antagonist of a regulatory sequence capable of altering expression of at least one streptococcal gene selected from: psaB, psaC, psaR, mntE, mgtA, and functional homologs thereof.

7. The composition of claim 1, wherein the killed bacteria were killed by at least one of: chemical treatment, thermal treatment, radiation, high hydrostatic pressure, pulsed electric field, ultrashort pulsed laser, ultrasound under pressure, and microbial inactivation.

8. The composition of claim 7, wherein the chemical inactivation comprises inactivation using:

(i) at least one of: a cross-linking agent, and an alkylating agent; or (ii) formalin; or (iii) beta-propiolactone; or (iv) at least one of: ultraviolet, photon, proton, heavy ion, and low-energy electron irradiation; or (v) gamma irradiation.

9. The composition of claim 1, wherein the attenuated or killed streptococcal bacteria:

(i) further comprise a defect in at least one streptococcal gene selected from: a gene encoding a DNA alkylation repair protein, a gene encoding hemolysin, a gene encoding pneumolysin, a gene encoding autolysin, and a gene encoding DNA polymerase IV; or (ii) further comprise a defect in at least one streptococcal gene selected from: adcR, cibAB, hexA, hexB, ply, luxS, lytA, mutS, prtA, radC, recA, recF, recN, recO, ritR, uvrA, uvrB, uvrC, uvrD, and functional homologs thereof; or (iii) are further modified to overexpress at least one of: PspA, PitA, PiuA, PiaA, AdcA, AdcAII, PhtA, PhtB, PhtD, PhtE, PcpA, CbpA, RrgA, RrgB, RrgC, StkP, and functional homologs thereof; or (iv) are not capable of producing a polysaccharide capsule.

10. The composition of claim 1, wherein the attenuated or killed streptococcal bacteria are of a single streptococcal species or serotype.

11. The composition of claim 1, wherein the attenuated or killed streptococcal bacteria comprise or consist of *Streptococcus pneumoniae* that are not psaA deletion mutants.

12. The composition of claim 1, wherein the attenuated or killed streptococcal bacteria comprise at least one of: *Streptococcus agalactiae, Streptococcus bovis, Streptococcus canis, Streptococcus dysgalactiae, Streptococcus equi, Streptococcus equinus, Streptococcus equisimilis, Enterococcus faecalis, Enterococcus faecium, Streptococcus iniae, S. milleri, Streptococcus mutans, Streptococcus pneumoniae, Streptococcus pyogenes, Streptococcus salivarius, Streptococcus sanguinis, Streptococcus suis*, and *Streptococcus uberis*.

13. The composition of claim 1, further comprising at least one of: an adjuvant, a pharmaceutically acceptable excipient, and a pharmaceutically acceptable carrier.

14. A method for inducing a cross-protective immune response in a subject against a plurality of serotypes from a given streptococcal species, the method comprising administering an effective amount of the composition of claim 1 to the subject to thereby induce the cross-protective immune response.

15. The composition of claim 1, wherein the composition does not comprise an adjuvant.

\*  \*  \*  \*  \*